(12) United States Patent
Lichtenstein

(10) Patent No.: US 11,576,560 B2
(45) Date of Patent: Feb. 14, 2023

(54) HOLLOW PROBE WITH SLEEVE

(71) Applicant: OTTek Ltd., Nazareth (IL)

(72) Inventor: Yoav Lichtenstein, Hod Hasharon (IL)

(73) Assignee: OTTek Ltd., Nazareth (IL)

( * ) Notice: Subject to any disclaimer, the term of this patent is extended or adjusted under 35 U.S.C. 154(b) by 314 days.

(21) Appl. No.: 16/756,920

(22) PCT Filed: Oct. 18, 2018

(86) PCT No.: PCT/IL2018/051115
§ 371 (c)(1),
(2) Date: Apr. 17, 2020

(87) PCT Pub. No.: WO2019/077609
PCT Pub. Date: Apr. 25, 2019

(65) Prior Publication Data
US 2021/0093157 A1    Apr. 1, 2021

Related U.S. Application Data

(60) Provisional application No. 62/574,221, filed on Oct. 19, 2017.

(51) Int. Cl.
*A61B 1/00* (2006.01)
*A61B 1/31* (2006.01)

(52) U.S. Cl.
CPC ........ *A61B 1/00151* (2013.01); *A61B 1/0014* (2013.01); *A61B 1/00066* (2013.01); *A61B 1/00135* (2013.01); *A61B 1/31* (2013.01)

(58) Field of Classification Search
CPC .............. A61B 1/00128; A61B 1/0014; A61B 1/00066; A61B 1/00151; A61B 1/00156; A61B 17/3431; A61B 1/00135
(Continued)

(56) References Cited

U.S. PATENT DOCUMENTS 2,406,600 A * 8/1946 Forestiere .............. A61B 17/42
                                                600/184
3,084,693 A * 4/1963 Cathcart ............ A61M 25/0119
                                                604/117
(Continued)

FOREIGN PATENT DOCUMENTS

DE         102007053288 A1      5/2008

OTHER PUBLICATIONS

International Search Report dated Jan. 31, 2019 for PCT/IL2018/051115 filed Oct. 18, 2018.
(Continued)

*Primary Examiner* — John P Leubecker
*Assistant Examiner* — Jae Woo
(74) *Attorney, Agent, or Firm* — Paul D. Bianco; Fleit Intellectual Property Law

(57) ABSTRACT

A hollow probe enabling insertion and accommodation of endoscopic and other instruments advancing within a lumen includes a central valve unit featuring a central bore and at least one valve for controlling the introduction and withdrawal of fluid into the central bore. A sliding tubular sheath is movably disposed inside the central valve unit. An impermeable flexible sleeve is sealingly anchored to the central valve unit and folds over to cover both the inside and outside of the sheath to sealingly envelop the sheath and contain the fluid, together with the valve unit, while allowing sliding of the sleeve-covered-sheath. An endoscope adapter is mountable to the proximal end of the sleeve-covered-sheath, for allowing insertion of the endoscope through the adapter into the sleeve-covered-sheath, includes at least one gasket for sealing at least one gap between the endoscope and the sleeve-covered-sheath for withholding fluids from escaping.

14 Claims, 32 Drawing Sheets

(58) Field of Classification Search
USPC .......................................................... 604/271
See application file for complete search history.

(56) References Cited

U.S. PATENT DOCUMENTS

| | | | |
|---|---|---|---|
| 3,866,601 A * | 2/1975 | Russell | A61B 1/00142 600/114 |
| 4,321,915 A | 3/1982 | Leighton | |
| 4,615,331 A * | 10/1986 | Kramann | A61B 1/273 600/114 |
| 4,765,314 A | 8/1988 | Kolditz et al. | |
| 4,871,358 A * | 10/1989 | Gold | A61M 25/0119 604/271 |
| 5,045,070 A | 9/1991 | Grodecki | |
| 5,163,927 A | 11/1992 | Woker | |
| 5,236,423 A | 8/1993 | Mix | |
| 5,259,364 A | 11/1993 | Bob | |
| 5,364,345 A | 11/1994 | Lowery | |
| 5,368,014 A * | 11/1994 | Anapliotis | A61B 1/00135 600/162 |
| 5,454,364 A | 10/1995 | Kruger | |
| 5,586,968 A * | 12/1996 | Grundl | A61B 1/31 600/114 |
| 5,676,688 A * | 10/1997 | Jaker | A61M 25/0119 606/198 |
| 5,797,835 A * | 8/1998 | Green | A61B 1/00147 600/113 |
| 5,902,286 A * | 5/1999 | Reitz | A61M 25/0119 604/271 |
| 6,077,219 A * | 6/2000 | Viebach | A61B 1/2736 600/114 |
| 6,217,569 B1 * | 4/2001 | Fiore | A61M 25/002 604/271 |
| 6,485,409 B1 | 11/2002 | Voloshin | |
| 6,503,192 B1 * | 1/2003 | Ouchi | A61B 1/00154 600/128 |
| 6,554,793 B1 * | 4/2003 | Pauker | A61B 1/00151 604/95.01 |
| 6,702,735 B2 | 3/2004 | Kelly | |
| 10,420,454 B2 | 9/2019 | Lichtenstein | |
| 2003/0114803 A1 | 6/2003 | Lerner | |
| 2003/0208223 A1 * | 11/2003 | Kleiner | A61B 17/3431 606/198 |
| 2004/0143161 A1 | 7/2004 | Baror | |
| 2004/0199121 A1 * | 10/2004 | Wenchell | A61B 17/3439 604/167.06 |
| 2004/0243144 A1 * | 12/2004 | Bonadio | A61B 1/00151 606/108 |
| 2005/0090717 A1 * | 4/2005 | Bonadio | A61B 17/0293 600/208 |
| 2005/0222582 A1 * | 10/2005 | Wenchell | A61B 1/313 606/108 |
| 2006/0020164 A1 * | 1/2006 | Butler | A61B 1/31 600/114 |
| 2006/0212063 A1 * | 9/2006 | Wilk | A61B 17/3421 606/191 |
| 2006/0224120 A1 * | 10/2006 | Smith | A61B 1/00154 604/167.01 |
| 2006/0252989 A1 | 11/2006 | Bar-Or | |
| 2006/0258909 A1 * | 11/2006 | Saadat | A61B 17/3431 600/121 |
| 2007/0260273 A1 * | 11/2007 | Cropper | A61B 1/00087 606/185 |
| 2008/0058595 A1 * | 3/2008 | Snoke | A61B 1/018 600/114 |
| 2008/0221390 A1 | 9/2008 | Bob | |
| 2009/0076464 A1 * | 3/2009 | Gresham | A61B 1/32 600/184 |
| 2009/0253967 A1 * | 10/2009 | Gill | A61B 1/00142 600/249 |
| 2010/0022958 A1 * | 1/2010 | Moreno, Jr. | A61B 1/00128 604/165.02 |
| 2010/0204546 A1 | 8/2010 | Hassidov | |
| 2010/0305557 A1 * | 12/2010 | Chu | A61B 1/012 606/27 |
| 2011/0065995 A1 * | 3/2011 | Cushner | A61B 1/00119 600/158 |
| 2011/0112359 A1 * | 5/2011 | Mark | A61B 1/00133 600/104 |
| 2012/0053410 A1 * | 3/2012 | Torisawa | A61B 1/126 600/114 |
| 2013/0237753 A1 * | 9/2013 | Mark | A61B 1/0014 600/104 |
| 2016/0278623 A1 | 9/2016 | Hirata | |
| 2017/0265724 A1 | 9/2017 | Lichtenstein | |
| 2019/0125176 A1 * | 5/2019 | Burt | A61B 1/00006 |

OTHER PUBLICATIONS

Written Opinion dated Jan. 31, 2019 for PCT/IL2018/051115 filed Oct. 18, 2018.
For International Application No. PCT/IL2015/051077 filed Nov. 9, 2015: International Search Report dated Feb. 10, 2016 Written Opinion dated Feb. 14, 2016 International Preliminary Examination Report dated Jul. 27, 2016.

* cited by examiner

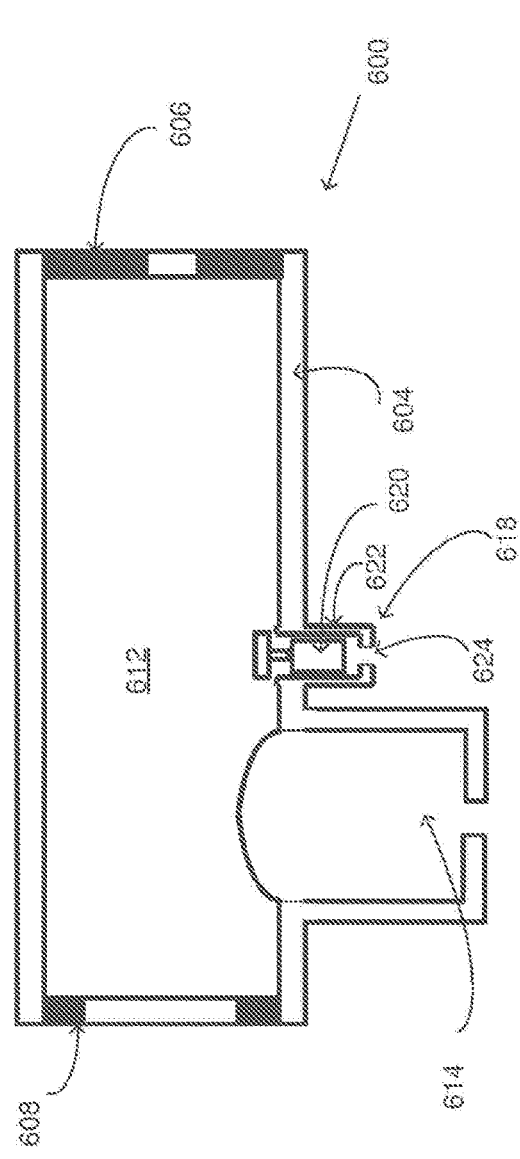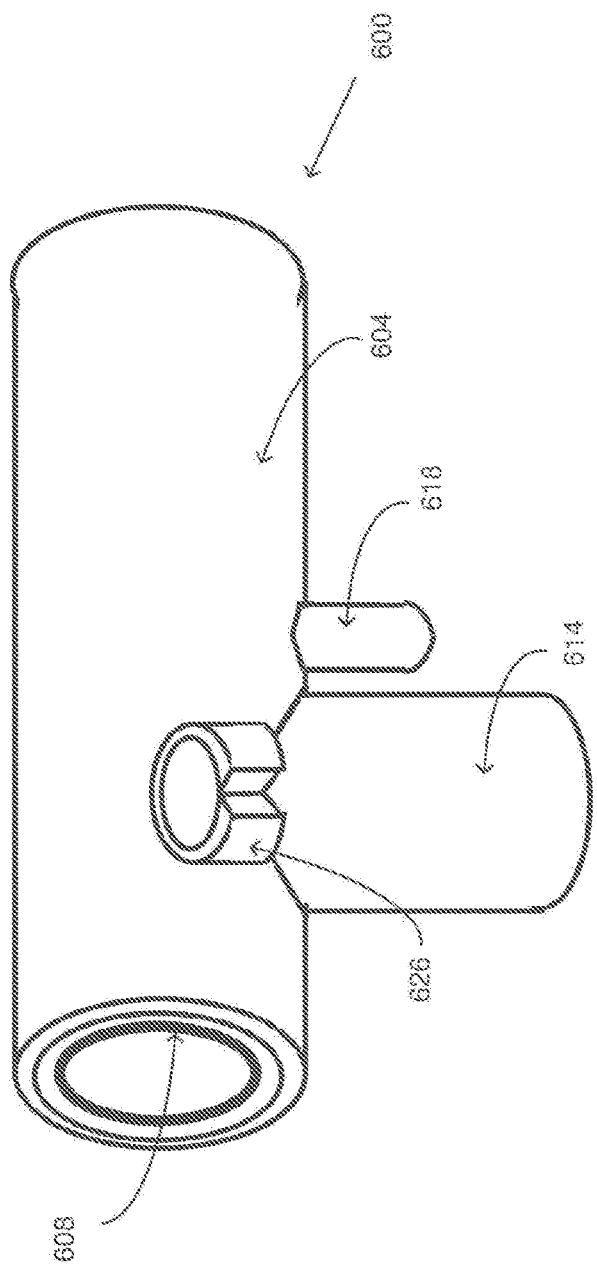
FIG. 24A
FIG. 24B

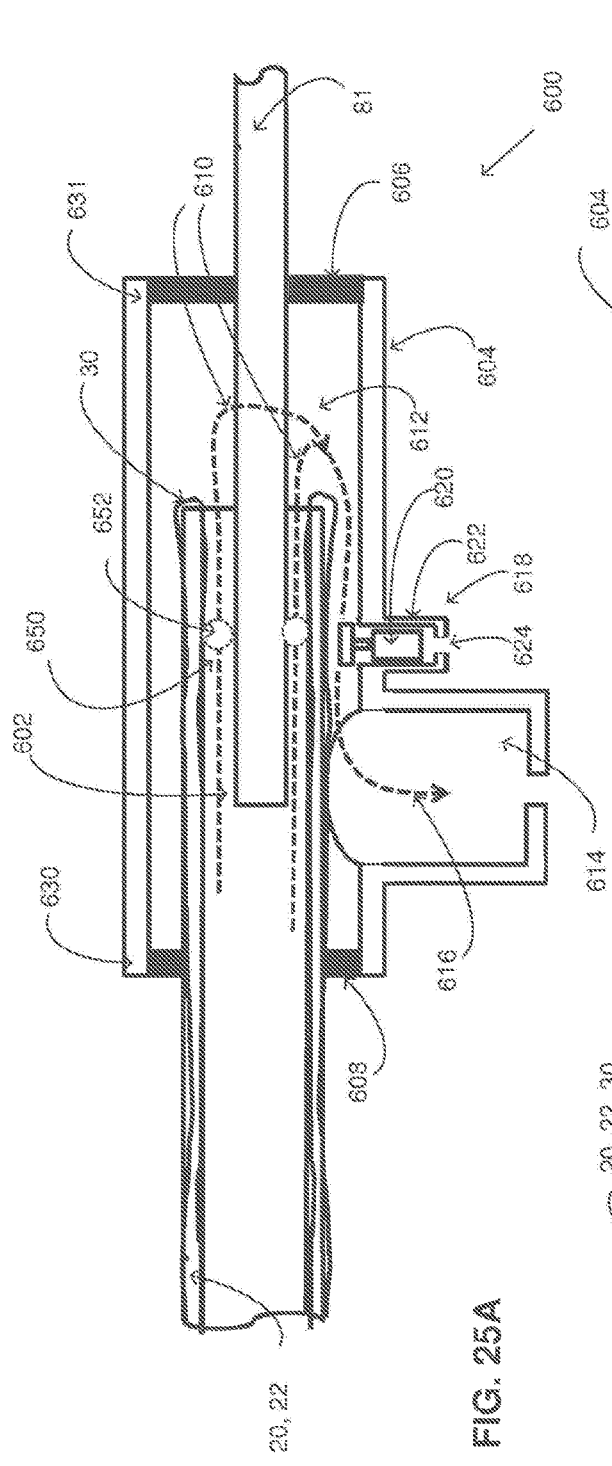
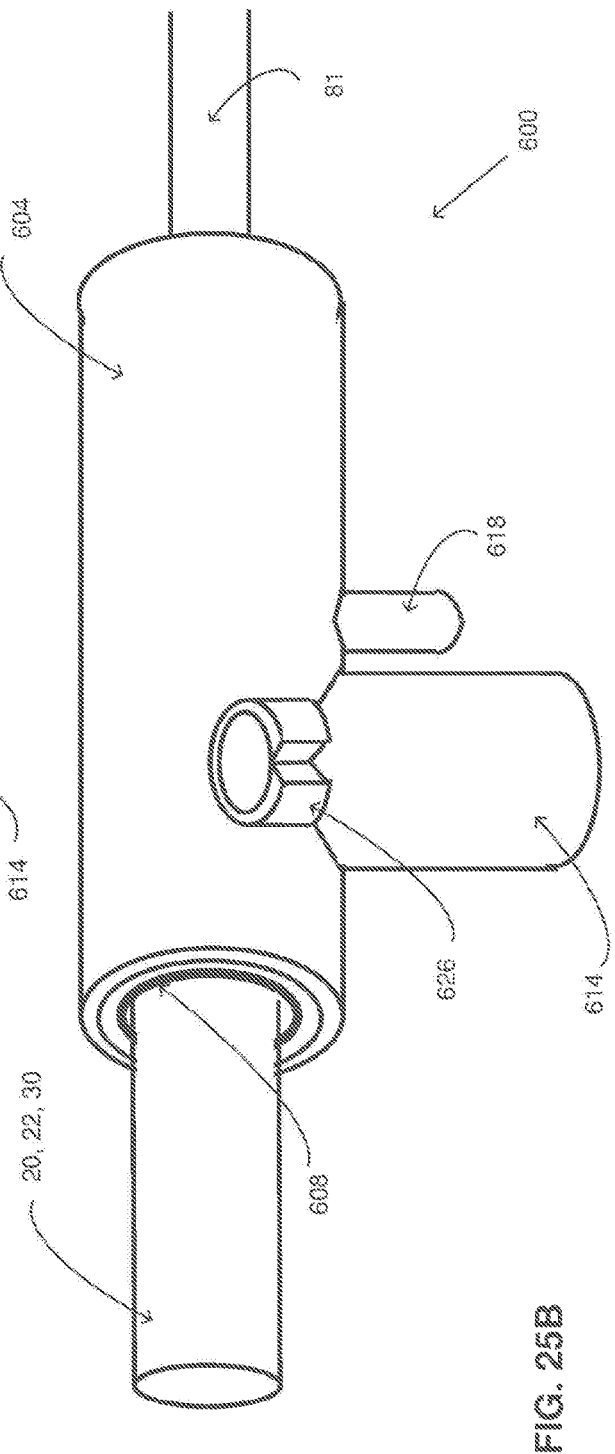
FIG. 25A
FIG. 25B

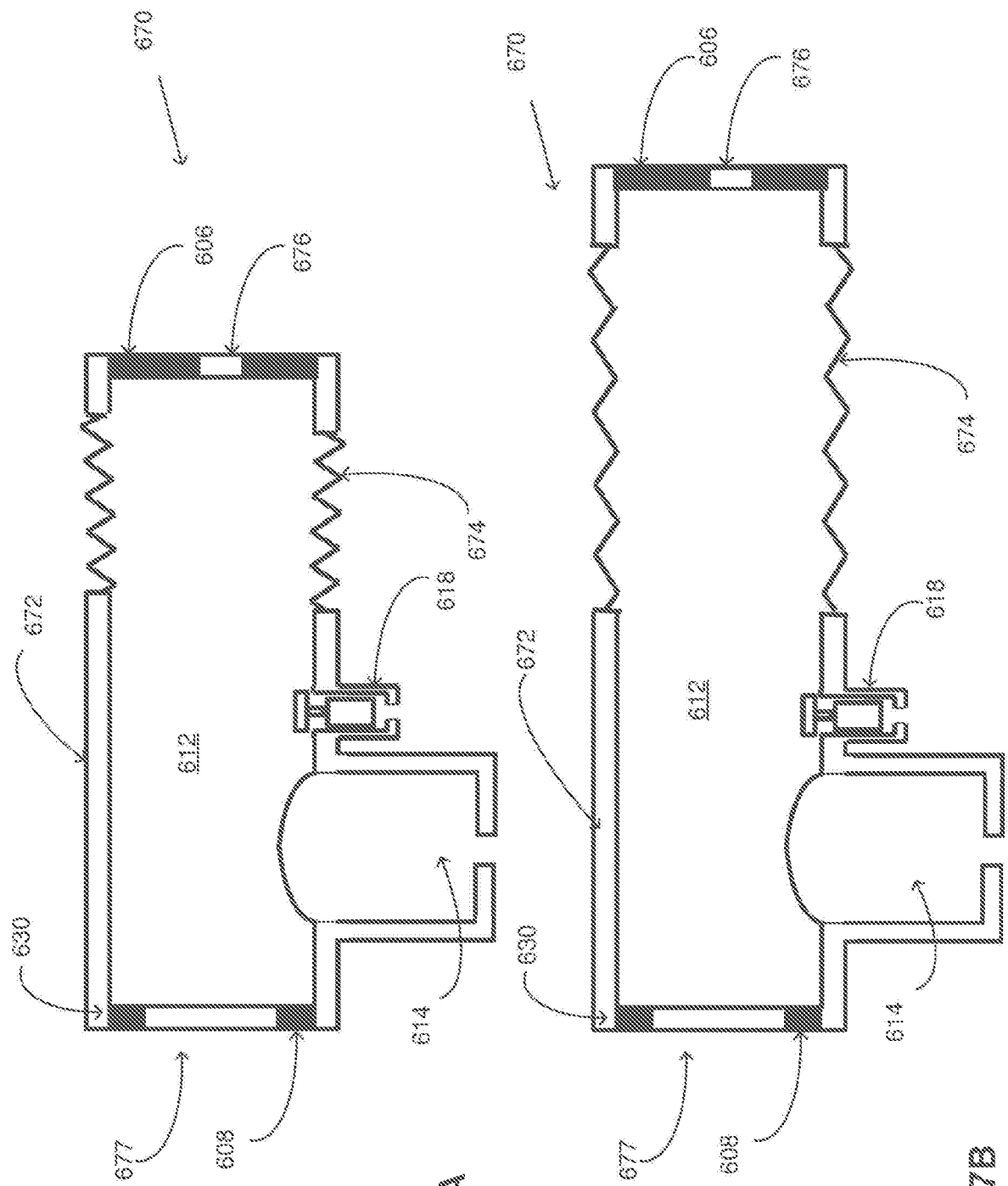

HOLLOW PROBE WITH SLEEVE

FIELD OF THE INVENTION

The present invention relates generally to the propulsion of objects within a lumen, and specifically to methods and devices for propelling medical instruments through a colon.

BACKGROUND OF THE INVENTION

The use of an endoscope for examining a body cavity is well known in the art. The diagnostic and therapeutic advantages conferred by direct examination of the gastrointestinal tract with a flexible endoscope have made this method a standard procedure of modern medicine. One of the most common endoscopic procedures is a colonoscopy, which is performed for a wide variety of purposes, including: diagnosis of cancer, determination of the source of gastrointestinal bleeding, viewing a site affected by inflammatory bowel disease, removing polyps, and reducing volvulus and intussusception.

While colonoscopies are useful and effective procedures, they are difficult for a physician to perform. Colonoscopies can be painful and include risks to the patient's long-term health. These problems stem from the need to push and steer a long, flexible colonoscope through the patient's intestine by pushing the colonoscope into the patient from the colonoscope's proximal side, located outside the patient's body.

It would therefore be desirable to provide a mechanism to facilitate insertion and extraction of an endoscope that lowers the risk of injury to the patient.

U.S. Pat. No. 4,615,331 to Kramman, entitled "Medical instruments with aid to introduction" disclose an elongated medical instrument for the examination or treatment of body cavities, in particular endoscopes, with a device to assist introduction by the principle of the tubular structure which becomes everted. The instrument includes a pipe 2 which is open at both ends and has pressure connectors 3 on the sides, and a flexible, eversible tubular structure 4 running through the pipe 2. The two ends 5, 6 of the tubular structure, each is connected to one end 7, 8 of the pipe 2, the medical instrument 9 runs through the pipe 2 inside the tubular structure 4, and the tubular structure 4 is folded in several double-layers in the region 10 of the distal end 11 of the medical instrument 9.

U.S. Pat. No. 6,702,735 to Kelly, entitled "Device for Movement Along a Passage" discloses a device for moving a tool along a passage, particularly for use in medical procedures, e.g. a colonoscope, which is surrounded by a sheath. The sheath has an inflatable region for engaging the passage wall, e.g. a colon. An annular extension region of the sheath is provided which becomes part of the inflated inflatable region, thereby increasing its length as the fluid pressure acts against a head of a tool to draw the tool along the passage. The annular extension region has sheath parts which face one another by their relative orientation caused by crumpling of the extension region, or the sheath parts are provided by folded portions. The extension region moves together with the tool as the sheath parts sequentially move into the inflated inflatable region. After inflation of the inflatable region of the sheath, inflation pressure acts against an inflatable head carried at the distal end region of the tool to draw the tool along the passage.

US Patent Application Publication No. 2008/0221390 to Konstantin, entitled "Medico-Technical Device Comprising a Self-Lubricating Element" discloses a technical medical device which can be engaged with a human or animal body while comprising a self-lubricating element, such as an everting tube, that is subjected to internal friction in the device, wherein at least one surface of the self-lubricating element is plasma-treated.

SUMMARY OF THE INVENTION

It is an object of some aspects of the present invention to provide an improved system and method for propelling an object within a lumen.

It is a further object of some aspects of the present invention to provide an improved propulsion mechanism for advancing an endoscope within a body cavity of a patient for purposes of examination, diagnosis, and/or treatment of the patient.

There is thus provided, in accordance with an embodiment of the present invention, a hollow probe which advances within a lumen. The probe enables insertion and accommodation of endoscopic and other instruments (herein, "endoscope"), The probe includes a central valve unit that features a central bore having a proximal end and a distal end, and at least one valve for controlling the introduction and withdrawal of fluid into the central bore. The probe further includes a sliding tubular sheath movably disposed inside the central valve unit, and a flexible sleeve, impermeable to the fluid and sealingly anchored to the central valve unit on both the distal and proximal ends. The sleeve is folded over to cover both the inside and outside of the sheath to sealingly envelop the sheath and contain the fluid, together with the valve unit, while allowing sliding of the sheath inside. An endoscope adapter is mountable to the proximal end of the sleeve-covered-sheath for allowing insertion of the endoscope there through into the sleeve-covered-sheath while sealing gaps between the adapter proximal side and the endoscope, and the gap between the adapter distal side and the sleeve-covered-sheath for retaining body fluids and preventing their leakage or escape through the gaps.

The endoscope adapter may include body fluids removal port for allowing removal, preferably by suction, of fluids (e.g., body fluids and or liquid and fecal particles, treatment and or washing liquids from the body) disposed in the cavity confined between the adapter, the endoscope and the sleeve-covered-sheath. The endoscope adapter may include a clutch, e.g., a clutch piston, for clasping the sheath sleeve in order to support the sheath covered sleeve while pushing or pulling the endoscope The endoscope adapter may feature an adapter housing sealingly (and releasably) mounted to the proximal end of the sleeve-covered-sheath. An endoscope accommodating sealing ring and a sheath sealing ring of the adapter housing may provide the required sealing of the adapter against the leakage of body fluids there from.

The adapter housing may further include a tubular shell that covers the proximal end of the sleeve-covered-sheath, wherein the shell includes at least two portions that can be releasably secured to each other to form the tubular shell and to be fastened around the sleeve-covered-sheath.

The adapter housing may further include a flexible tubular portion that allows extension and contraction thereof to facilitate free insertion and retraction movement of the endoscope within the sleeve-covered-sheath while keeping a distal sealing end of the housing sealingly engaging the sheath sleeve, and/or a proximal end of the housing sealingly engaging the endoscope.

The adapter may be sealingly coupled to a proximal end of the valve unit, and may further include a flexible portion that allows extension and contraction thereof to facilitate free insertion and retraction movement of the endoscope within the sleeve-covered-sheath and the adapter. The flexible portion may feature a flexible proximal or distal portion of the adapter, or sealingly couple a distal end of a housing of the adapter and a proximal end of the valve unit.

An endoscope handle fastening fixture for allowing placement of an endoscope handle, may be mounted on the adapter housing for convenience of the user.

In accordance with another aspect of the present invention, there is thus provided, a method for propelling a hollow probe within a lumen, wherein the probe enables insertion and accommodation of endoscopic and other instruments ("endoscope"). The method includes inserting a flexible sleeve within a tubular sheath, sliding the sheath through a central bore of a central valve unit, folding over a proximal sleeve portion and a distal sleeve portion of the sleeve inside out over both ends of the sheath to cover both the inside of the sheath and the outside of a proximal sheath portion and a distal sheath portion of the sheath, sealingly anchoring the proximal sleeve portion to a proximal bore end of the central bore and the distal sleeve portion to a distal bore end of the central bore, such that the sleeve together with the valve unit sealingly envelop the sheath, inserting a distal tip portion of the sleeve-covered-sheath into the lumen, and advancing and retracting the sheath within the lumen while maintaining the sheath covered by the sleeve. The method further includes sealing the gap between the sleeve-covered-sheath and the endoscope adapter, which is mountable to the proximal end of the sleeve-covered-sheath and sealing the gap between the endoscope and the endoscope adapter, while allowing insertion of the endoscope through the adapter into the sleeve-covered-sheath, for retaining body fluids from escaping through the gaps.

The procedure of sealing may include removing body fluids disposed in the cavity confined between the adapter, the endoscope, and the sleeve-covered-sheath, through a body fluids removal port, a clutch (e.g., with a piston) for clasping the sheath sleeve in order to support the sheath covered sleeve while pushing or pulling the endoscope.

The procedure of sealing may include (releasably) sealingly mounting an adapter housing to the proximal end of the sleeve-covered-sheath. The procedure of sealingly mounting may further include sealing the housing with an endoscope accommodating sealing ring and a sheath sealing ring.

The procedure of sealingly mounting may further include covering the proximal end of the sleeve-covered-sheath by releasably securing two-portions of a tubular shell to each other and fastening around the sleeve-covered-sheath. The procedure of sealingly mounting may further may include mounting a housing featuring a flexible tubular portion that allows extension and contraction thereof to facilitate free insertion and retraction movement of the endoscope within the sleeve-covered-sheath while keeping a distal end of the housing sealingly engaging the sheath sleeve, and/or a proximal end of the housing sealingly engaging the endoscope The procedure of sealingly mounting may further include sealingly coupling the adapter to a proximal end of the valve unit, and/or sealingly coupling by a flexible portion that allows extension and contraction thereof to facilitate free insertion and retraction movement of the endoscope within the sleeve-covered-sheath and the adapter.

The method may further include the procedure of selectively placing an endoscope handle over an endoscope handle fastening fixture mounted on the endoscope adapter.

BRIEF DESCRIPTION OF THE DRAWINGS

The present invention will be understood and appreciated more fully from the following detailed description taken in conjunction with the drawings in which:

FIGS. 24A and 24B are a schematic cross-sectional illustration and a schematic isometric illustration, respectively, of an embodiment of an endoscope adapter, constructed and operative in accordance with the invention;

FIGS. 25A and 25B are a schematic cross-sectional illustration and a schematic isometric illustration, respectively, of the endoscope adapter of FIGS. 24A and 24B, when mounted on a sleeve-covered-sheath and conveying an endoscope there through;

FIGS. 27A and 27B are schematic isometric illustrations, of a modification of the endoscope adapter of FIGS. 24A and 24B, exemplifying a contracted state and an extended state, respectively;

DETAILED DESCRIPTION OF THE EMBODIMENTS

Figure 1:
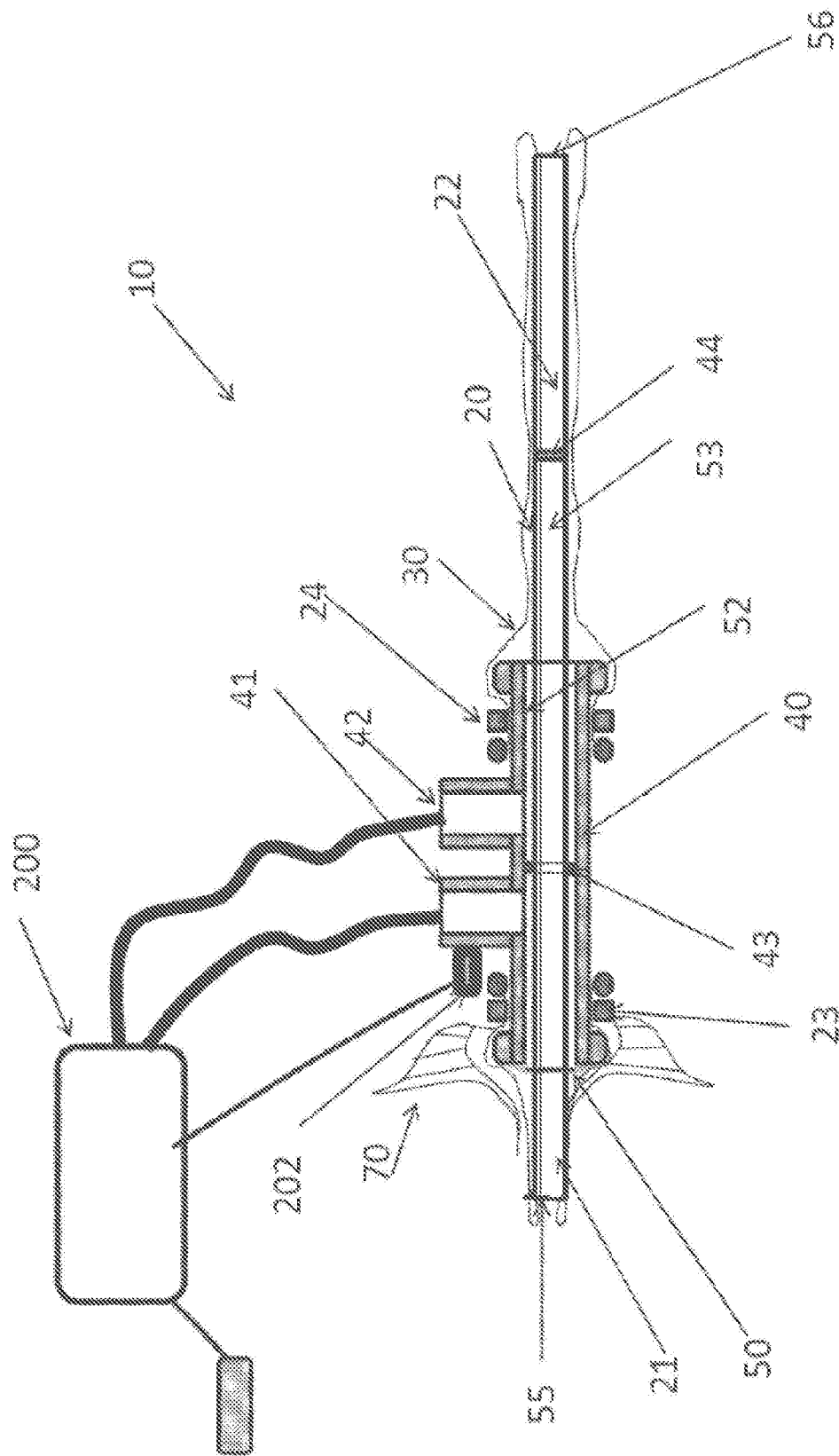
FIG. 1 is a schematic, cross-sectional illustration of an embodiment of a dual-valves endoscopic probe with flexible sleeve, constructed and operative in accordance with the invention.

In preferred embodiments of the present invention, a hollow probe is advanced through the lower gastrointestinal tract of a patient, by optionally inflating a flexible sleeve coupled to the probe. The probe includes a tubular sheath, and the flexible sleeve is inserted within the sheath and inverted over the sheath tips to envelop the sheath when wrapping both the external and the internal faces of the sheath. Both ends of the sleeve are anchored, at intermediate locations around the sheath to an external central valve unit, typically disposed adjacent to the patient's anus during operation. The sleeve, together with the valve unit, sealingly envelop the sheath. In other words, the central valve unit encircles the sheath at some intermediate portion thereof, and the anchored sleeve externally enshrouds the other sheath portions (proximal and distal), and enfolds internally to envelop the entire internal tubular cavity of the sheath, while leaving an internal passage within the sleeve allowing insertion of medical examination, diagnosis and treatment equipment, and tools, such as an endoscope, there through. The sleeve is impermeable to a fluid that can be introduced there into through the valve unit. The sleeve, together with the valve unit, sealingly envelop the sheath and contain the introduced fluid, while allowing sliding of the sheath. As the sleeve is inflated by the fluid, preferably using gas, pressurized gas (including air) or liquid, the probe is propelled forward. Simultaneously or alternatively, the sheath can be pushed manually on its proximal side, or by some mechanized propulsion. Optionally, is no liquid is introduced into the sleeve (by the choice of the operator or if no liquid supply is available), the arrangement of the sheath within a sleeve can still be fully operational (e.g. by letting free flow of ambient air into the sleeve through the valve unit), requiring conventional push and pull action of the sleeve-covered-sheath within the lumen, while the sleeve retains its protective no-rubbing characteristic as it is not sliding against the wall of the lumen due to its anchoring to the valve unit. The inflation of the flexible sleeve can be controlled, so that the sleeve is fed out of the sheath gradually. A portion of the sleeve that is inflated expands radially outward and remains substantially stationary relative to the intestinal wall as long as the sleeve is inflated, without rubbing the intestinal wall, avoiding frictional damage thereto and facilitating frictionless movement within the gastrointestinal tract. The probe can thereby be advanced or retracted (inserted and extracted) more easily, and trauma to the gastrointestinal tract is minimized.

The flexible sleeve can be pushed forward by a push-pull rod, or pulled back by an extra wire connected to the flexible sleeve, or with the application or mechanical propulsion.

The central bore of the probe can include separate steering for easing the maneuvering of the probe over or around curves in the gastrointestinal tract and obstructions, such as, blood clots, small deformations and other obstacles, so that the probe can move within the patient's body while further minimizing harmful contact and friction. Any suitable steering methods known in the art may be used.

The probe's central bore can also accommodate tools and instruments for examination, diagnosis and treatment of the patient, such as an endoscope, and such instruments may also be embedded in the sheath or inserted beside the probe—between the sheath and the sleeve or on the sleeve. Preferably, the instruments include an endoscopic instrument—an imaging device, such as, a miniature video camera and light source, as are known in the art, which are used to capture endoscopic images, and therefore the terms "probe", "hollow probe" and "endoscopic probe" are interchangeably used herein, while the term "endoscope" refers to tools or instruments that are accommodated through the central bore of the endoscopic hollow probe, or in an alternative location or the probe. Accessories for operating the instruments and receiving data therefrom can include wires, fiber-optic lines, or tubes which are coupled to the instruments and extend to an operator or to equipment outside of the patient, which operates the instruments and receives or transmits data therefrom. The wires, line or tubes preferably pass through the central bore of the probe and out through the central valve unit. Wireless instruments may also be used.

Figure 7:
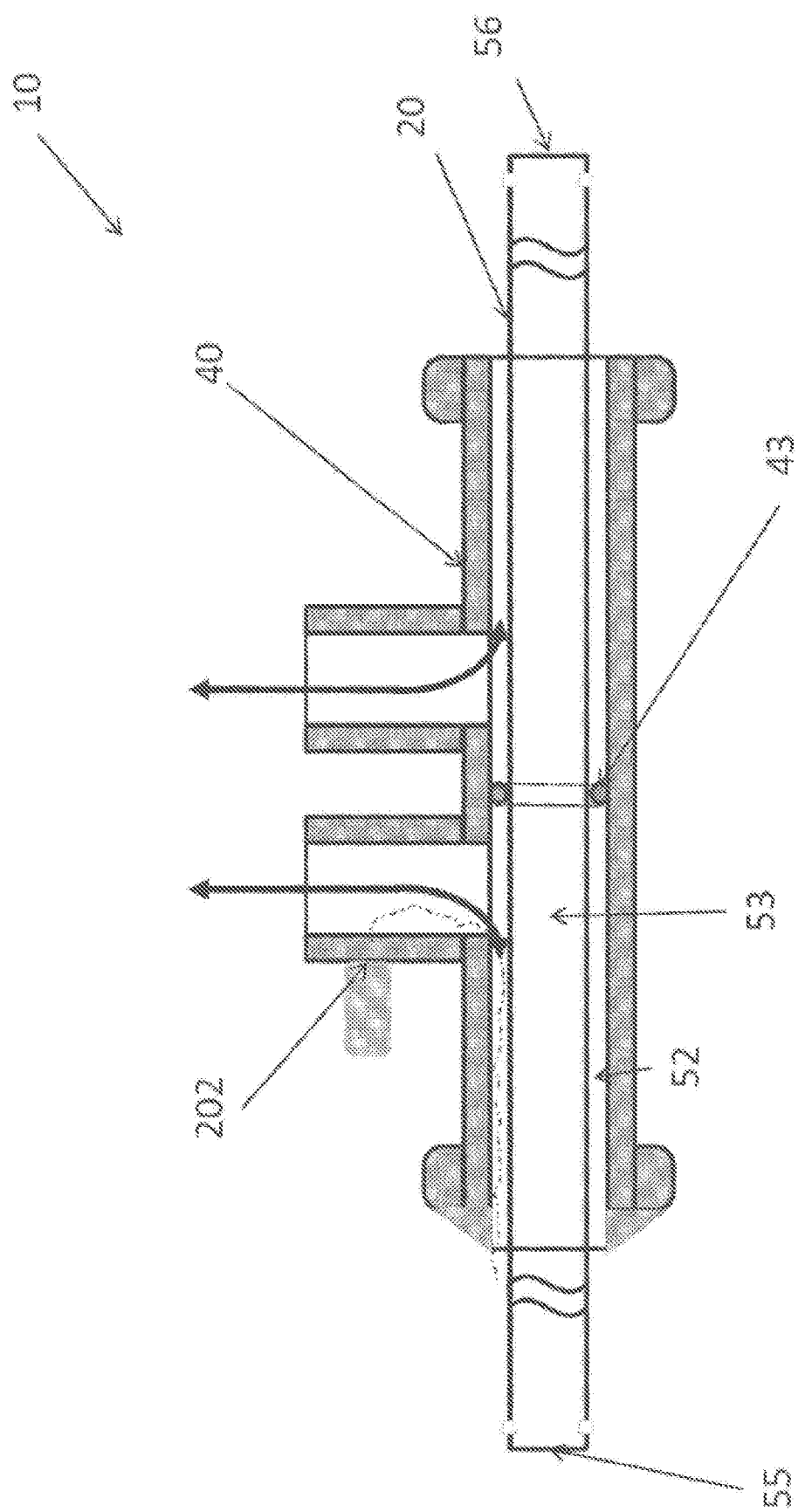
FIG. 7 is a schematic, cross-sectional illustration of an embodiment of a central valve unit featuring dual valves configured for the embodiment of FIG. 1.

Reference is now made to the Figures, in which like numbers designate like parts. FIG. 1 is a schematic, cross-sectional illustration of an embodiment of a dual-valves endoscopic probe 10 with flexible sleeve, constructed and operative in accordance with the invention. Reference is also made to FIG. 7, which is a schematic, cross-sectional illustration of central valve unit 40 featuring dual valves configured for probe 10. Probe 10 includes a central valve unit 40. The distal end 50 of central valve unit 40 is connected to anus adaptor 70. Probe 10 also includes flexible sheath 20 that is configured to slide within central bore 52 of central valve unit 40. Sheath 20 preferably has a hollow tubular shape, with an external diameter which is smaller than the diameter of interior bore 52 of central valve unit 40, allowing free slide movement of sheath 20 within bore 52. Sheath 20 has a central bore or tubular cavity 53. Optionally, insertion and accommodation of instruments for examination, diagnosis and treatment of the patient can be within bore 52, and in some instances, also within bore 53. Probe 10 further includes sleeve 30 which is preferably made from a flexible, biocompatible plastic material, of any suitable type known in the art, and is further preferably impermeable to fluids that may be contained therein. Sleeve 30 preferably has a wall thickness between approximately 0.1 and 0.4 mm and an overall diameter of approximately 15 mm when inflated. Sleeve 30 is inserted within and along tubular cavity 53, and is folded over sheath 20 at tips 55, 56 of sheath 20, and thereby inverted to cover distal portion 21, and proximal portion 22 of sheath 20, and is sealingly and tightly fastened to both sides of central valve unit 40 by anchorings 23 and 24. Sleeve 30, together with valve unit 40 sealingly envelop sheath 20, which is completely enshrouded by sleeve 30 and valve unit 40, with its central tubular cavity 53 left open for insertion and accommodation of tools and instruments for examination, diagnosis and treatment of the patient there through, while the instruments are maintained isolated from the internal face of sheath 20 (namely, the wall of sheath tubular cavity 53) by sleeve 30.

The central hollow bore 53 of probe 10 (the interiors of central valve unit 40 and sheath 20) enables the insertion and extraction of medical treatment or diagnostic tools, and/or other mechanisms within the interior of probe 10, e.g., mechanisms used for easing the movement of sleeve 30 within sheath 20.

Sleeve 30 typically has an unfolded length of approximately 3 meters. Sheath 20 typically has a length of approximately 1.5 meters. Sleeve 30 can be folded in a way so that the length of folded sleeve 30 is still greater than the length of sheath 20.

Preferably, probe 10 includes steering capabilities, which can be included as part of a diagnostic tool. The steering capabilities can include steering mechanisms, as are known in the endoscopic art, such as, mechanisms that rely on the use of pull-wires for steering. Examples of such steering units are described herein below with reference to FIGS. 17 and 18.

Central valve unit 40 enables the controlled intake and outtake of a fluid, liquid or gas, into the interior volume of folded sleeve 30, keeping sheath 20 totally immersed in the fluid.

Forward illumination 202, including wiring as in FIG. 7, may be inserted between sheath 20 and bore 52 for facilitating inspection around distal edge 55 of distal portion 21 of sheath 20 when inserted within colon 101 of human body 100, and sleeve 30 (and sheath 20, if required) may be sufficiently transparent to allow illumination therethrough. In this context it is noted that tools, sensors, endoscopes, and/or instruments for examination, diagnosis and treatment of the patient may be disposed in least one of a variety of locations, including within central bore 53 of sheath 20 outside sleeve 30, within central bore 53 of sheath 20 within sleeve 30 (inserted between sheath 20 and sleeve 30), embedded in sheath 30 as exemplified in FIG. 16, deployed beside sheath 20 within sleeve 30 (inserted between sheath 20 and sleeve 30) as exemplified by forward illumination 202 in FIGS. 7, 10, 11, 13 and 14, and deployed beside sheath 20 outside sleeve 30.

Figure 2:
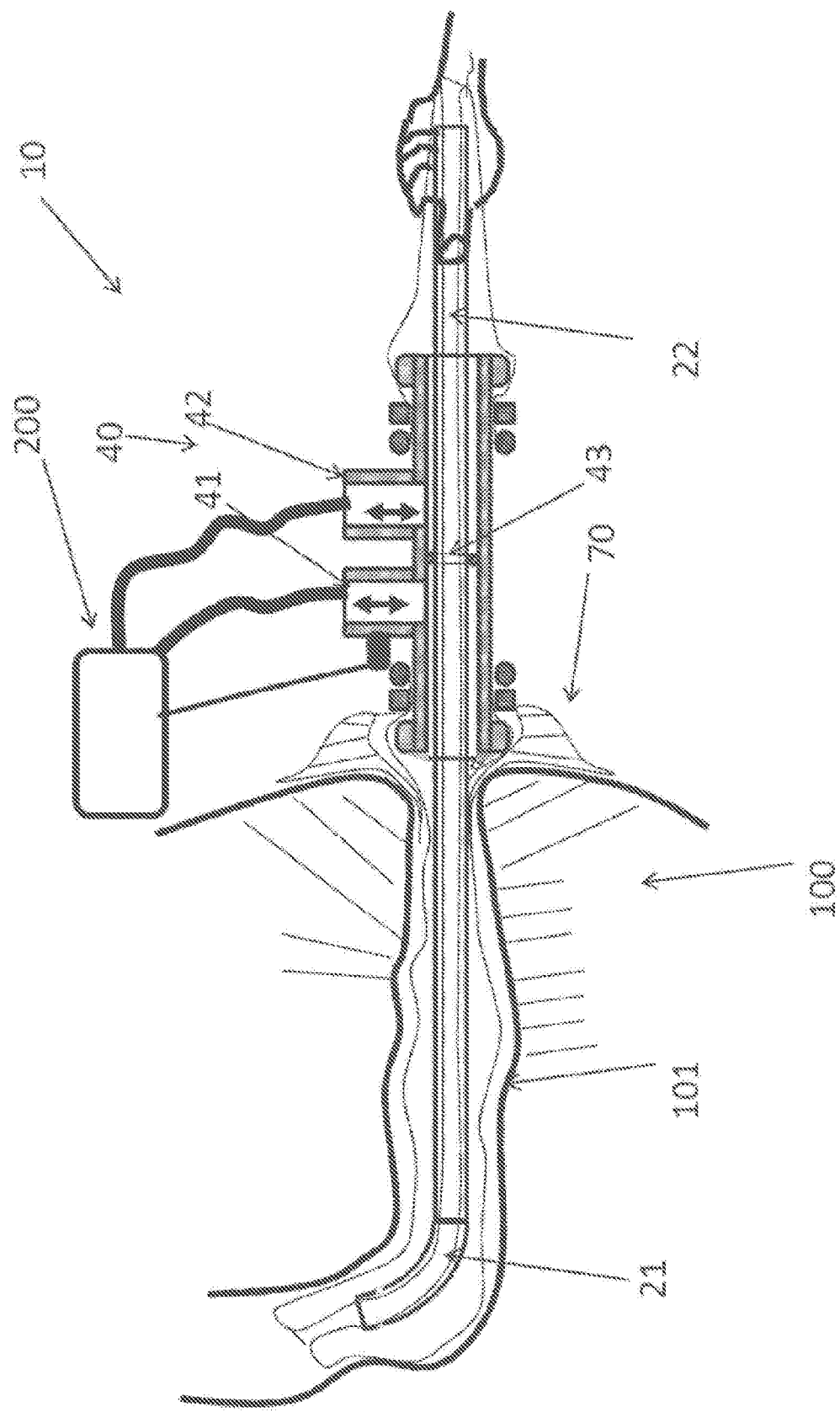
FIG. 2 is a schematic, cross-sectional illustration of the probe of FIG. 1 while inserted in a patient's body.

Reference is now made also to FIG. 2. FIG. 2 is a schematic, cross-sectional illustration of probe 10 being used in an endoscopic examination of a patient's colon 101, while inserted in a patient's body 100. Probe 10 is inserted into colon 101 through the patient's anus. A liquid or gas fluid pump/supplier 200 is then actuated by opening the relevant valve, for example distal valve 41 or proximal valve 42, depending on whether insertion or extraction is desired. When insertion is desired, fluid is pumped through valve 41 into the distal portion of sleeve 30 covering sheath 20. Pump/supplier 200 is coupled to a source of liquid, or a regulated, pressurized source of gas, such as, carbon dioxide ($CO_2$) or any other suitable gas. Preferably, a gas pressure in the range of approximately 0.3 ATM is used to inflate sleeve 30. Alternatively, a liquid, such as sterile water, may be used to inflate sleeve 30. The inflated portion of sleeve 30 typically expands radially and may contact the interior wall of colon 101, but there is generally only minimal or no longitudinal motion of sleeve 30 against the wall of colon 101. Thus, rubbing and trauma to the intestinal wall are minimized. The expansion of the inflated portion of sleeve 30 pulls its internally inserted part within bore 53 of sheath 20 at the expense of the remainder of sleeve 30 about the proximal portion 22 of sheath 20, thereby the mere shortening of the proximal part of sleeve 30 can be used to push sheath 20 further into human colon 101. During such insertion procedure into human colon 101, the fluid within proximal portion of flexible sleeve 30 covering proximal portion 22 is allowed to withdraw through valve 42), to nullify excess fluid resistance.

Figure 3:
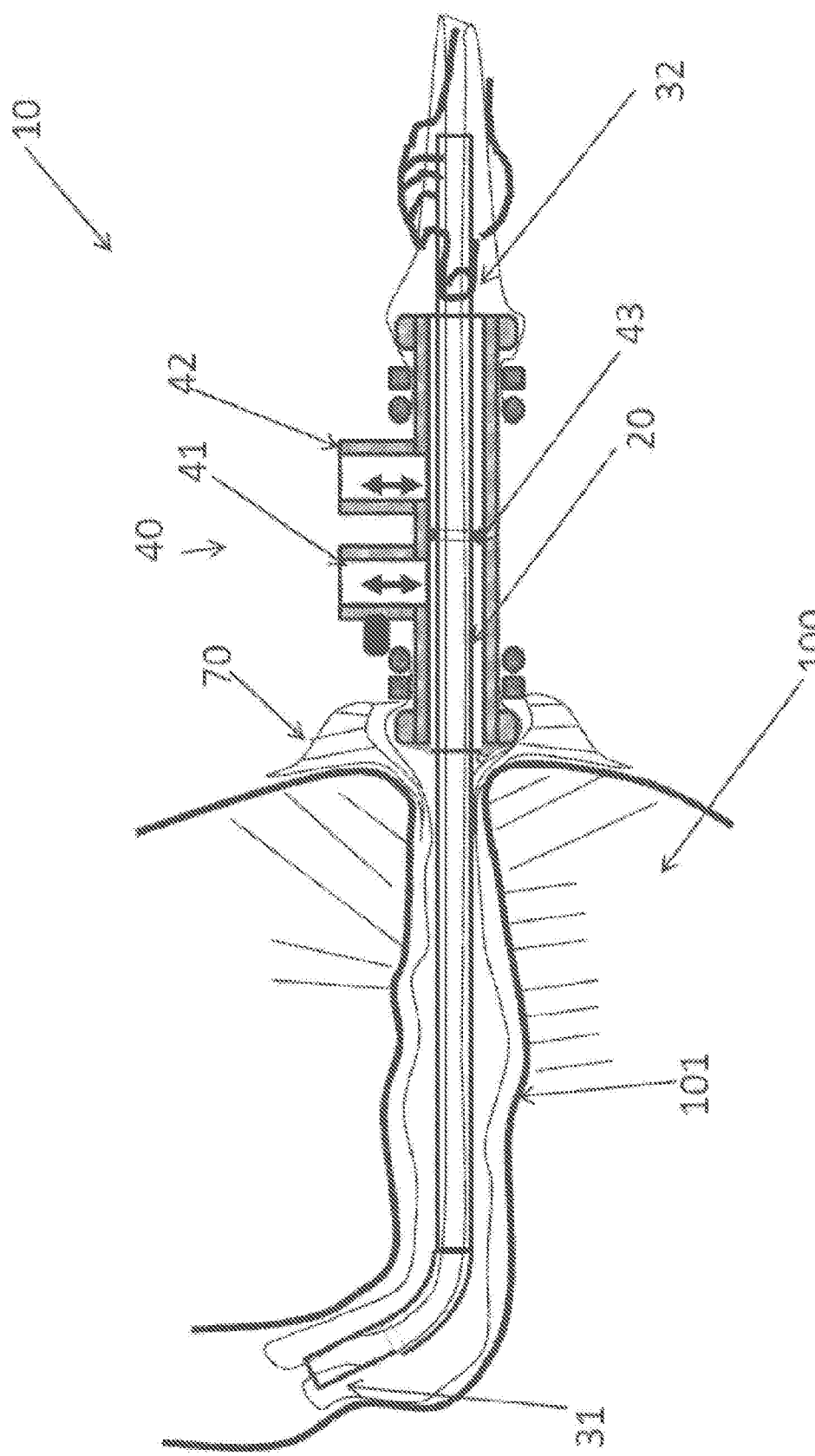
FIG. 3 is a schematic, cross-sectional illustration of the probe of FIG. 2 with its sheath inserted further into the patient's body.

Reference is now made also to FIG. 3, which is a schematic, cross-sectional illustration of the probe 10 with sheath 20 inserted further into the patient's body (colon 101). to advance probe 10 further along the interior of colon 101, a distal part 31 of sleeve 30 is inflated by opening valve 41 and pushing a liquid or gas through it into the interior of sleeve 30. As a result, the distal part 31 of sleeve 30 will extend/expand beyond the distal edge of sheath 20 into and against the interior wall of colon 101. Sheath 20 can then be manually pushed toward distal part 31 of sleeve 30. The configuration of a long sleeve squeezed along sheath, typically results in minimal or completely nil fluid passage between sheath internal side (bore 53) and sleeve 30 that passes inside bore 53, because of the pressure of the endoscopic probe, or the pressure of another instrument that squeeze them together, or because sleeve 30 is tightly folded over the sheath ends 55, and 56. Simultaneously to the manual pushing of sheath 20, a pedal can be actuated in order to supply additional liquid or gas to distal part 31 of sleeve 30 in order to further push and advance sleeve 30 along the interior of colon 101. At the same time the liquid or gas that is present or has leaked back to the proximal end of the sleeve through a separating mechanism, such as, separation O-ring 43, that is utilized to block the flow or passage of fluid directly from valve 41 to valve 42, (allowing passage only past edges 55 and 56, and along the entire length of sleeve 30 within bore 53, if it is possible) can be extracted from proximal part 32 of sleeve 30 (through valve 42). Similarly, an optional internal separating blocking element 44 (which can also feature an O-ring) can be placed, selectively or throughout the entire session, anywhere within bore 53 to press sleeve 30 against the internal face of bore 53 and thus hermetically block passage of fluid past edges 55 and 56, and along the entire length of sleeve 30 within bore 53, if such a passage is not blocked anyways as noted above. Element 44 can be integral with sleeve 30. Element 43 alone (in case passage of fluid within and between sleeve 30 and bore 53 is insignificant or not possible), or the two blocking element, 43 and 44 (as much as element 44 is required to block passage of fluid within and between sleeve 30 and bore 53), create two completely isolated pockets which can be separately inflated and deflated, using the two distinct valves, 41 and 42. Advance of sleeve 30 inside sheath 20 toward the distal edge of sheath 20 can be supported by a suitable mechanism, such as, a push-pull rod, alone or combined with medical instrumentation (described below with reference to FIGS. 4 and 9, and an endoscope described below with reference to FIGS. 24A to 29).

In order to avoid perforation of sleeve 20, particularly at its distal side 31, a diagnostic tool, which can be included as part of or separate from the push-pull rod, is used to monitor the distance between distal edge 55 of sheath 20 and distal part 31 of sleeve 30.

To retract probe 10 from colon 101, the proximal part 32 of sleeve 30 is inflated by opening valve 42 and pushing liquid or gas through it into the interior of sleeve 30. At the same time, the liquid or gas can be extracted from distal part 21 of sleeve 30 through valve 41, causing sleeve 30 to expand/extend beyond the proximal edge 56 of sheath 20. A portion of sleeve 30 can then be manually folded over the proximal edge of sheath 20. Sheath 20 is then extracted from colon 101 by pulling manually on sheath 20 away from distal part 21 of sleeve 30.

Simultaneously to the manual pulling of sheath 20, a pedal can be actuated in order to supply additional liquid or gas to proximal part 32 of sleeve 30 in order to further push and advance sleeve 30. At the same time, the liquid or gas that is present in, or has leaked from proximal part 32 to the distal part 31, can be extracted from distal part 31 of sleeve 30 (through valve 41).

After an endoscopic examination is complete, the pressure in sleeve 30 can be relieved, and sleeve 30 deflated, for a relatively quick retraction of probe 10. In this case probe 10 can be withdrawn from colon 101 by pulling on sheath 20.

Probe 10 can feature a rod, which can be selectively inserted within the central bore of sheath 20. The rod may be used for various purposes. The rod may include at least one of: bulbous head for facilitating push/pull of sleeve 30, expandable head for facilitating push/pull of sleeve 30, expandable head for selectively blocking fluid flow in sleeve 30 at a blocking location disposed within bore 53 of sheath 20 (functioning as blocking element 44), and instruments used for examination, diagnosis and treatment of the patient.

Figure 4:
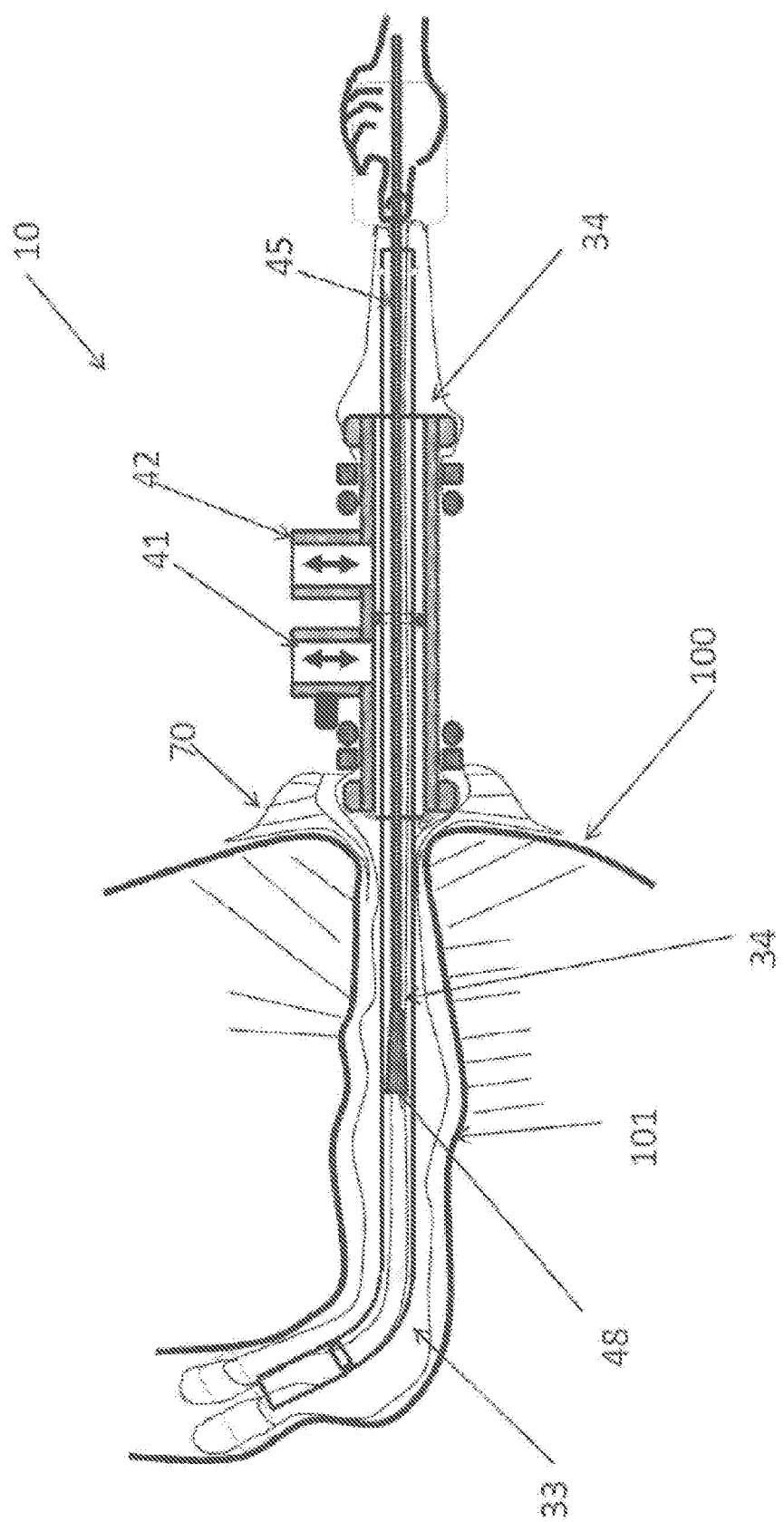
FIG. 4 is a schematic, cross-sectional illustration of the probe of FIG. 3 with a push-pull rod for assisting insertion and/or extraction of the probe.
Figure 9:
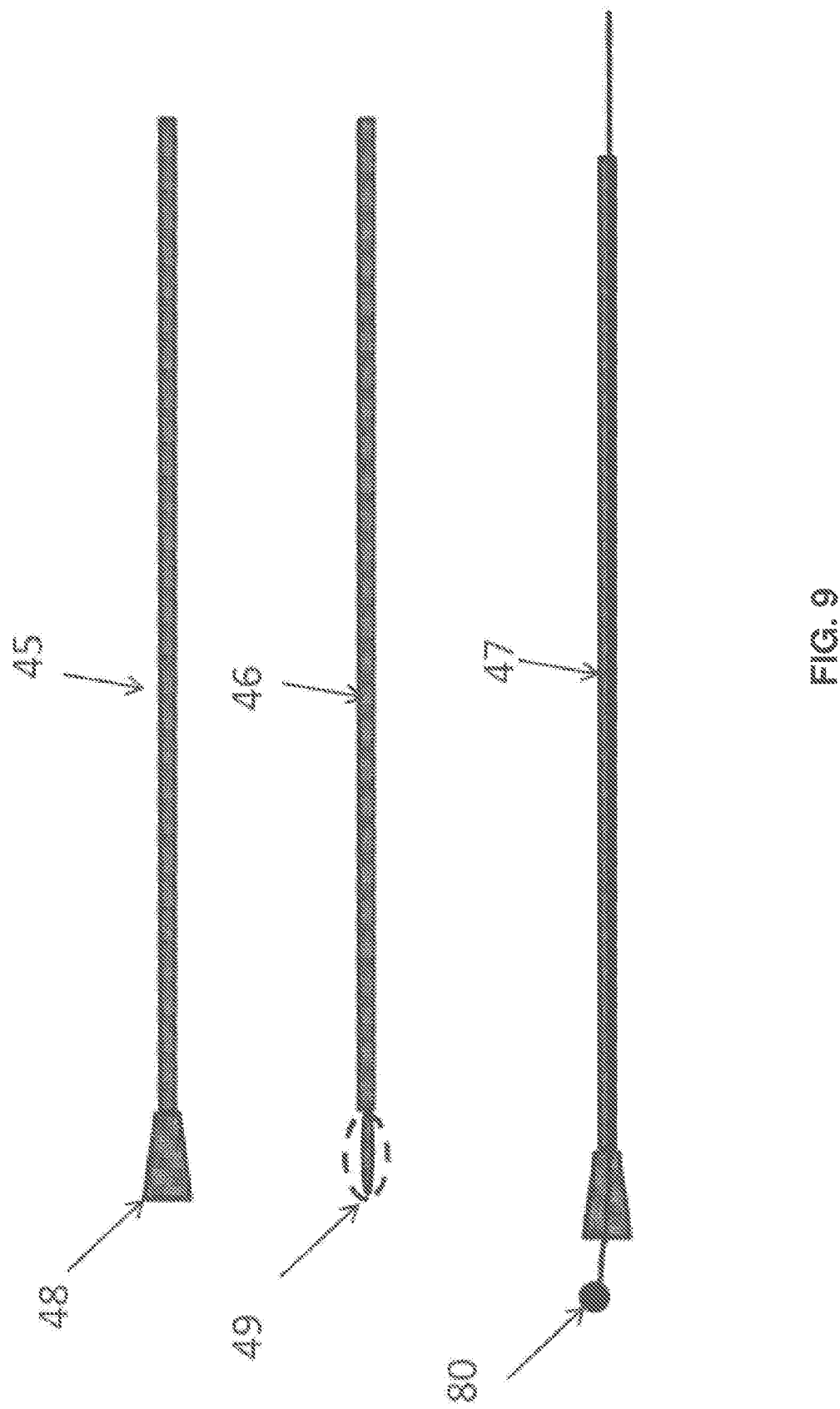
FIG. 9 includes schematic illustrations of embodiments a push-pull rod, a push-pull rod with inflatable and deflatable head, and a combination push-pull rod/diagnostic tool configured for operation in conjunction with an endoscopic probe with flexible sleeve, constructed and operative in accordance with the invention.

FIG. 4, Is a schematic, cross-sectional illustration of probe 10 illustrating a steering mechanism for assisting insertion and/or extraction of probe 10, such as, a push-pull rod 45, used to advance sleeve 30 inside sheath 20 toward the distal edge of sheath 20 during insertion or toward the proximal edge of sheath 20 during extraction. A portion, preferably head 48, of push-pull rod 45 can be sized with a diameter that will cause push-pull rod 45 to put sleeve 30 in contact with sheath 20. This contact can seal a portion of sleeve 30 against sheath 20 to create fluid seal separating the volume contained within sleeve 30 in to two pockets: a proximal pocket 34 and a distal pocket 33, and prevent the passage of air from one section of sleeve 30 (pocket 33) to another (pocket 34) (pockets 33, 34 overlap sides 31, 32, correspondingly, but may also extend to partially occupy the other side—such as pocket 34 extending from side 32 toward side 31, depending on the location of head 48). This can assist a user to control which sections of sleeve 30 are inflated. Push-pull rod 45 can include a mechanism for adjusting the size of a portion of its diameter, such as an inflatable and deflatable head 48. Reference is now made also to FIG. 9. FIG. 9 includes schematic illustration of embodiments of push-pull rod 45 with head 48, push-pull rod 46 with inflatable and deflatable head 49, and a combination push-pull rod/diagnostic tool 47 configured for operation in conjunction with an endoscopic probe with flexible sleeve, constructed and operative in accordance with the invention. Push-pull rod 45 includes head 48, and push-pull rod 46 includes inflatable head 49 that help facilitate the pushing and pulling of sleeve 30 inside sheath 20. Pushing and pulling of push-pull rod 45 or 46 can be synchronized with the inflation and deflation of inflatable head 48. The inflation of head 49 within sheath 20 can be progressed to the extent of sealingly clasping the inner portion of sleeve 30 within bore 53 to the inner face of sheath 30 and prevent passage of fluid through sleeve 30 at this sealing location. Push-pull rod 47 combines a diagnostic tool 80 (similar to diagnostic tool 80 of FIG. 5) and a push-pull rod (similar to push-pull rod 45) to provide a combination of a diagnostic tool and a push-pull rod.

Figure 5:
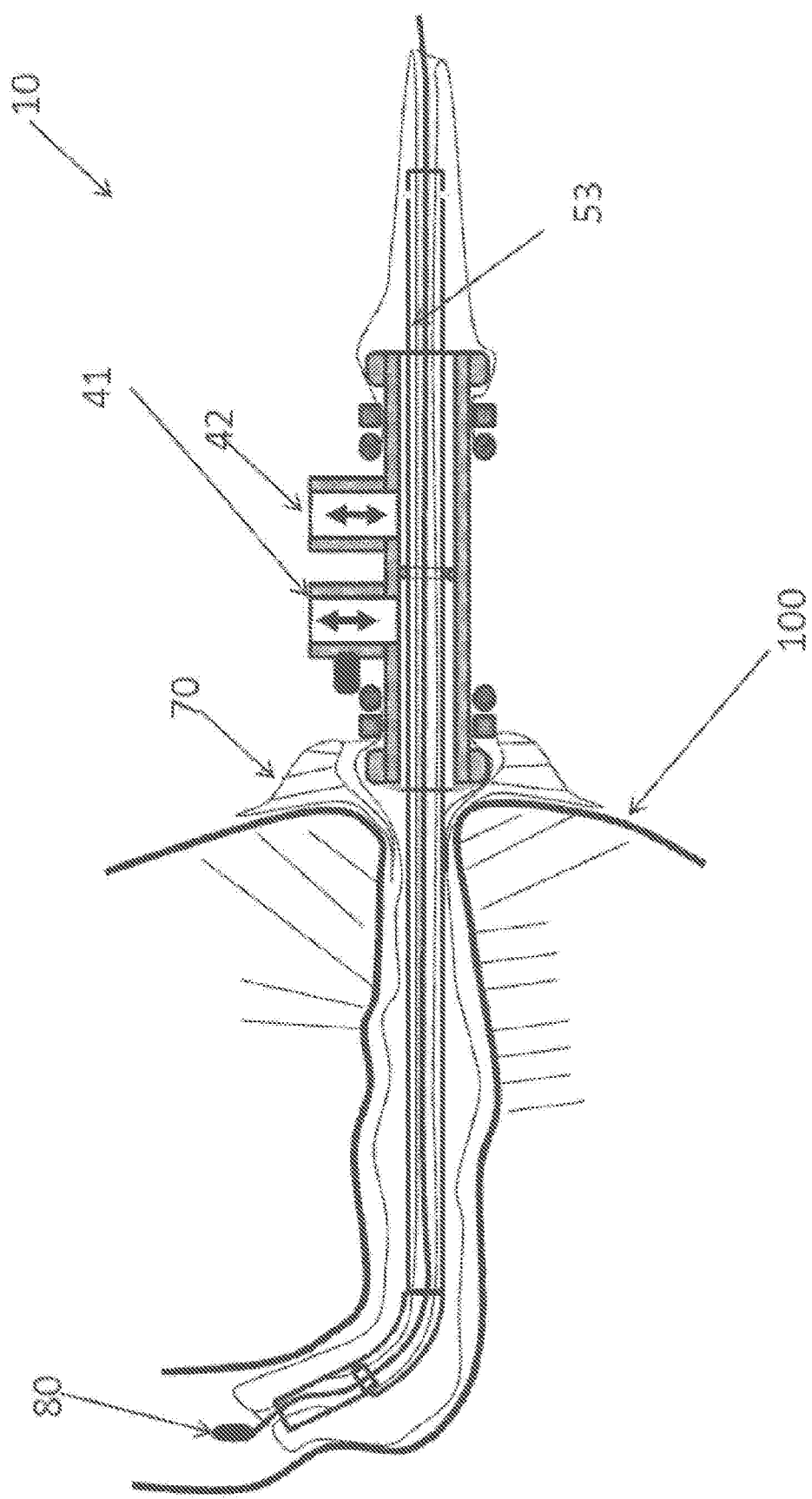
FIG. 5 is a schematic, cross-sectional illustration of the probe of FIG. 3 with a diagnostic tool inserted in the central bore of the probe.

FIG. 5, is a schematic, cross-sectional illustration of probe 10 illustrating a diagnostic tool 80 inserted in the central bore 53 of sheath 20 and probe 10. While inserting treatment or diagnostic tool 80 through the central bore 53, sleeve 30 can be deflated to ease the insertion of the tool 80 (e.g. by extracting any excess fluid, liquid or gas, remaining in the interior of sleeve 30 through valve 41 and/or 42). Deflation of sleeve 30 may involve complete extraction of fluid therefrom to the extent sleeve 30 is tightly adhered by the internal vacuum created within sleeve 30 to both sides of sheath 20, rendering both into an overtube-like configuration (sleeve 30-"coated" sheath 20). Such a configuration leaves the widest possible clear passage within bore 53 for convenient insertions and retractions of diagnostic tools or instruments, such as used, for instance, in polyp removal surgery.

It is noted that when sleeve 30 is inflated and is advanced or retracted in conjunction with, or for the sake of, advancing or receding sheath 20 within colon 101, the portion of sleeve 30 disposed within bore 53 advances/retracts twice the length sheath 20 advances/recedes, and is typically clenched inwardly about the central axis of bore 53. As a result, any object inserted through sleeve 30, such as tool 80 in FIG. 5 (particularly its cable or rod), or rod 45 in FIG. 4, is firmly grasped by the inflated, inwardly clenching, sleeve 30, which typically grasps and carries the inserted object twice the length by which sheath 20 progresses (to either direction). Accordingly, to avoid over-progression of the inserted object, sleeve 30 can be deflated, intermittently—if required, for allowing an offsetting reverse push or pull of the inserted object within bore 53, compensating for its already-occurred or prospective over-progression.

Diagnostic tool 80 can also include: suction and/or irrigation ports, sensors of various types and/or specially adapted surgical instruments, such as, biopsy forceps. These elements are known generally in the art, and are not shown in the figures. Substantially any other suitable type of tool or sensor may be adapted with tool 80 and coupled to an external apparatus by the appropriate adaptation of its cable (or rod) to the central bore 53 of probe 10.

Figure 6:
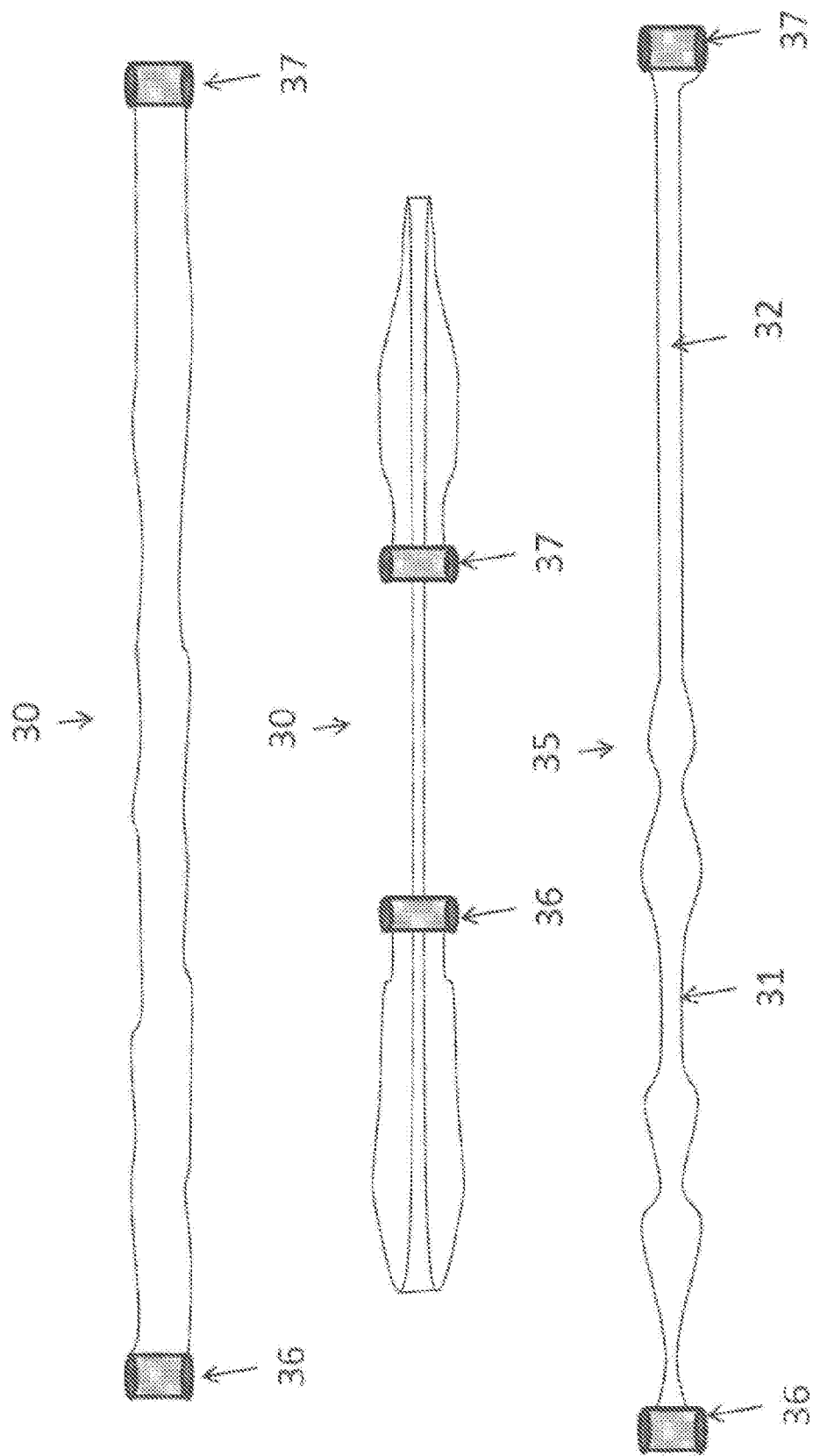
FIG. 6 includes schematic illustrations of embodiments of a flexible sleeve in folded and un-folded modes, and a variable diameter flexible sleeve, constructed and operative in accordance with the invention.

FIG. 6 includes schematic illustrations of embodiments of flexible sleeve 30 in folded and un-folded modes, and variable diameter flexible sleeve 35, constructed and operative in accordance with the invention. In certain embodiments, sleeves 30, 35 can have different properties or characteristics for different parts of the sleeve. For example, the (plastic or nylon) material on one or both ends 36, 37 of sleeve 30 can be thinner or thicker than other portions of the sleeve. The sleeve can also feature varying diameters on one or more portion of the sleeve. Sleeve 35, has a variable diameter on its distal side 31, that matches variations in the colon, and a fixed diameter that matches the sheath's (outer, or both outer and inner) diameter on its proximal side 32 (the side that does not reach the colon).

Figure 8:
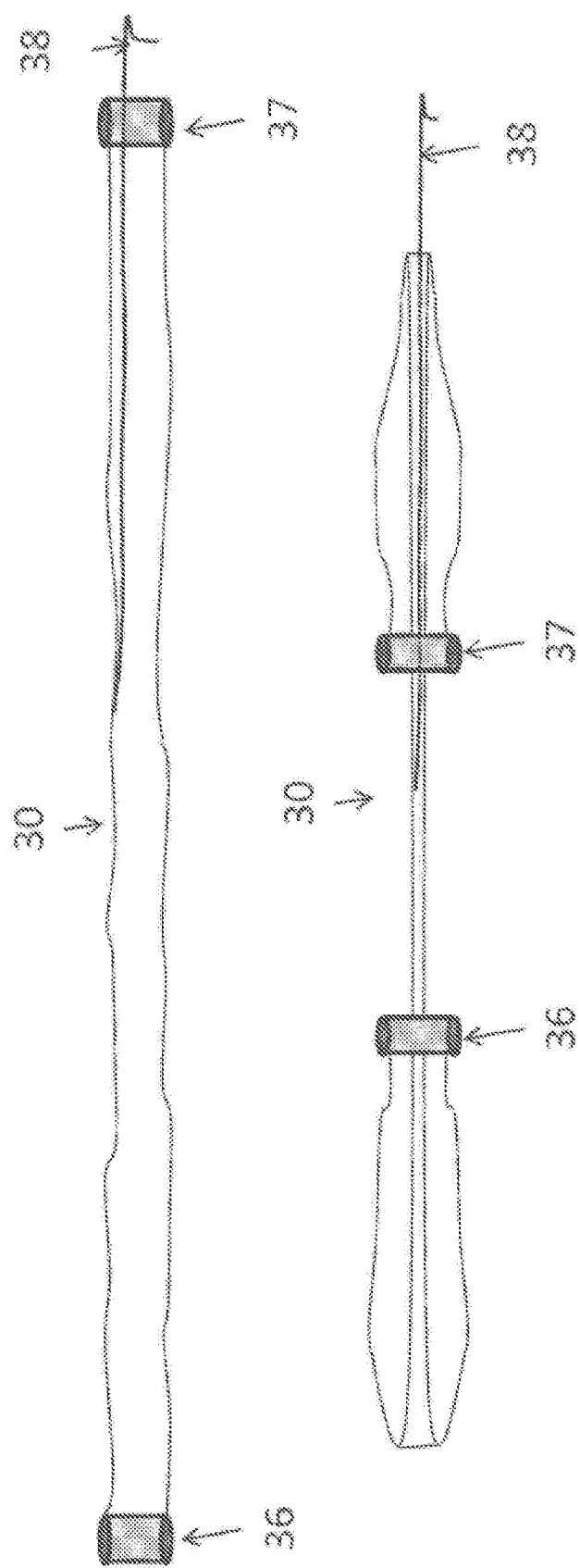
FIG. 8 includes schematic illustrations of an embodiment of a flexible sleeve constructed and operative in accordance with the invention with puling wire for assisting retraction of the sleeve.
Figure 10:
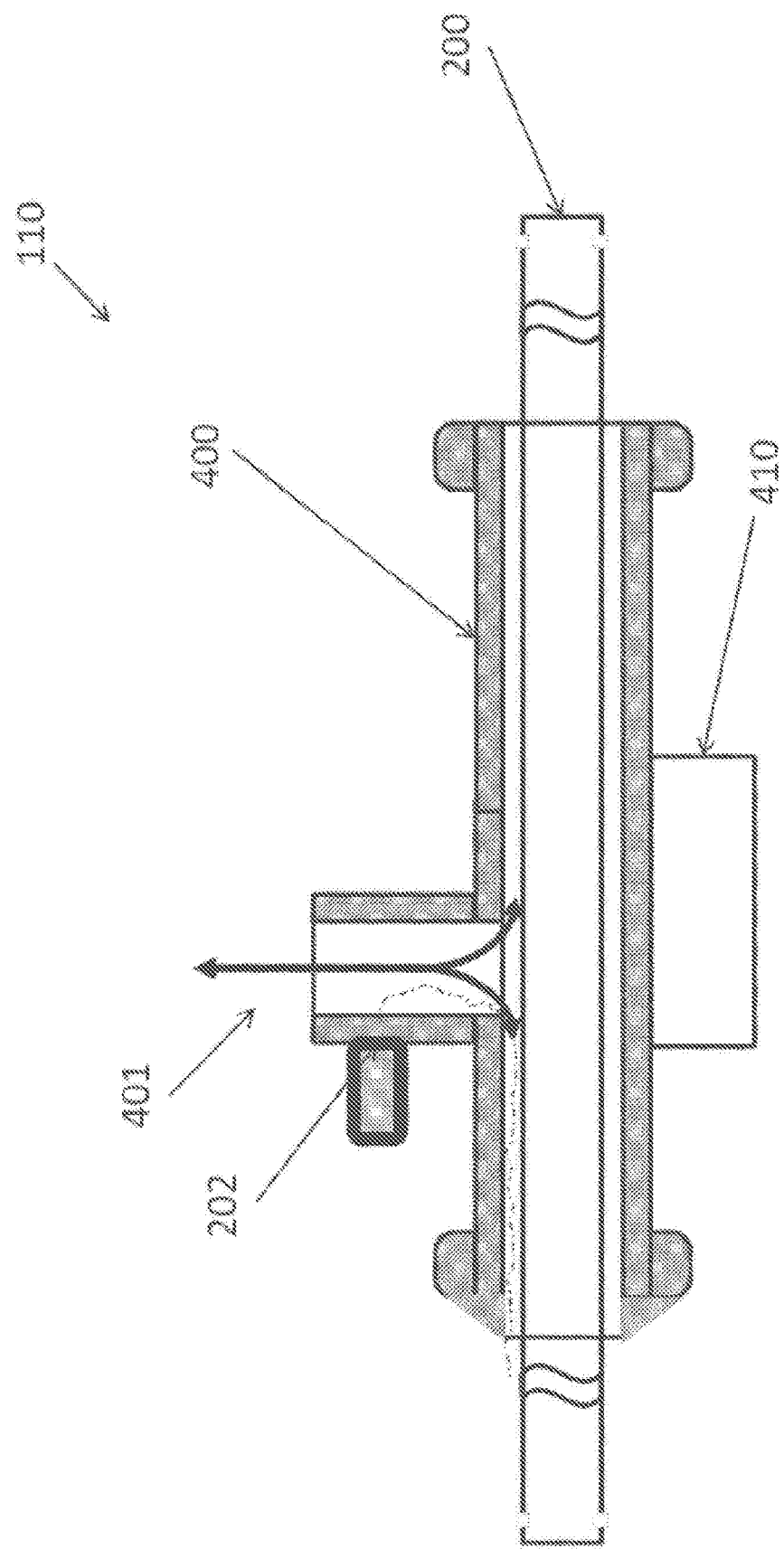
FIG. 10 is a schematic, cross-sectional illustration of an embodiment of a single-valve endoscopic probe, constructed and operative in accordance with the invention.

FIG. 8 includes schematic illustrations of an embodiment of flexible sleeve 30 constructed and operative in accordance with the invention with puling wire 38 for assisting retraction of sleeve 30. When sleeve 30 is require to be retracted within sheath 20, pulling wire 38 can be used to advance sleeve 30 inside sheath 20 towards proximal edge of sheath 20 by pulling on wire 38. FIG. 10 is a schematic, cross-sectional illustration of an embodiment of single-valve endoscopic probe 110, constructed and operative in accordance with the invention. Probe 110 is similar to probe 10 of FIG. 1, wherein single-valve unit 400 is applied instead of the dual valve unit 40. Single valve unit 400, includes valve 401 and allows filling or withdrawal of fluid from sleeve 30 in its entirety, without discriminating between the distal or proximal portions of sleeve 30. Accordingly, the advancement or retreat of sheath 20 within colon 101 is not performed with the aid of selective filling with fluid of the relevant portion of sleeve 30, and the sheath propulsion is either completely manual or conducted by further propulsion by unit 410

Figure 11:
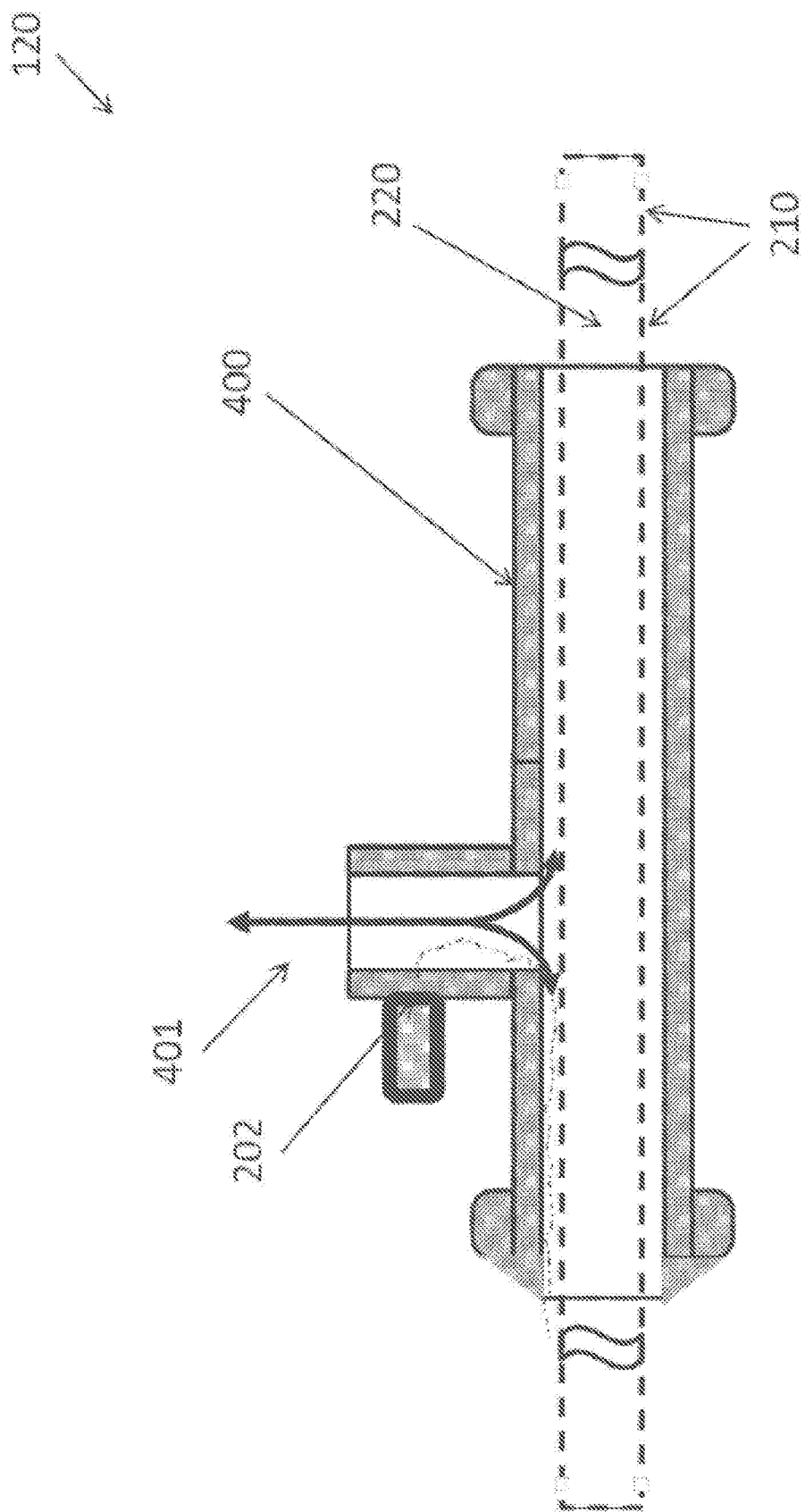
FIG. 11 is a schematic, cross-sectional illustration of an embodiment of a single-valve endoscopic probe, constructed and operative in accordance with the invention, featuring a perforated sheath.

FIG. 11 is a schematic, cross-sectional illustration of single-valve endoscopic probe 120, constructed and operative in accordance with the invention, featuring perforated sheath 220 (the sleeve is not shown). The perforation of sheath 220, represented by holes 210, allows easy passage of fluid, liquid or gas, within the sleeve through holes 210, allowing an almost uninterrupted flow within the sleeve, despite the obstruction of sheath 220 to a uniform, omnidirectional flow of fluid within the sleeve, for fast inflating and deflating of the sleeve.

Although shown with the single-valve unit 400 (and without the sleeve), the alternative sheaths and sleeves of FIGS. 11-14 can be utilized with the dual-valve unit 40 of FIG. 1.

Figure 13:
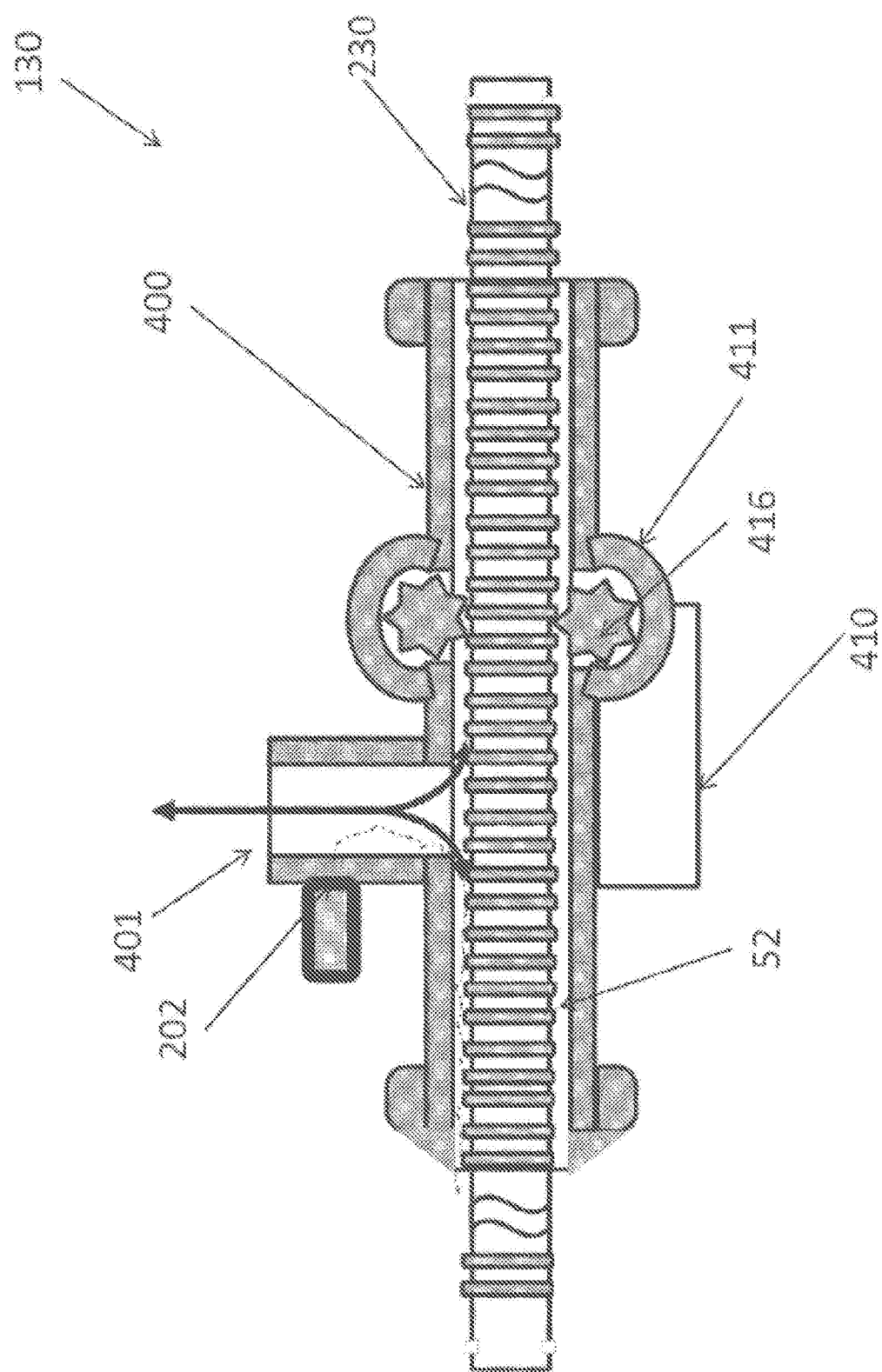
FIG. 13 is a schematic, cross-sectional illustration of an embodiment of a single-valve endoscopic probe, constructed and operative in accordance with the invention, featuring a grooved sheath and an advancing gear.
Figure 14:
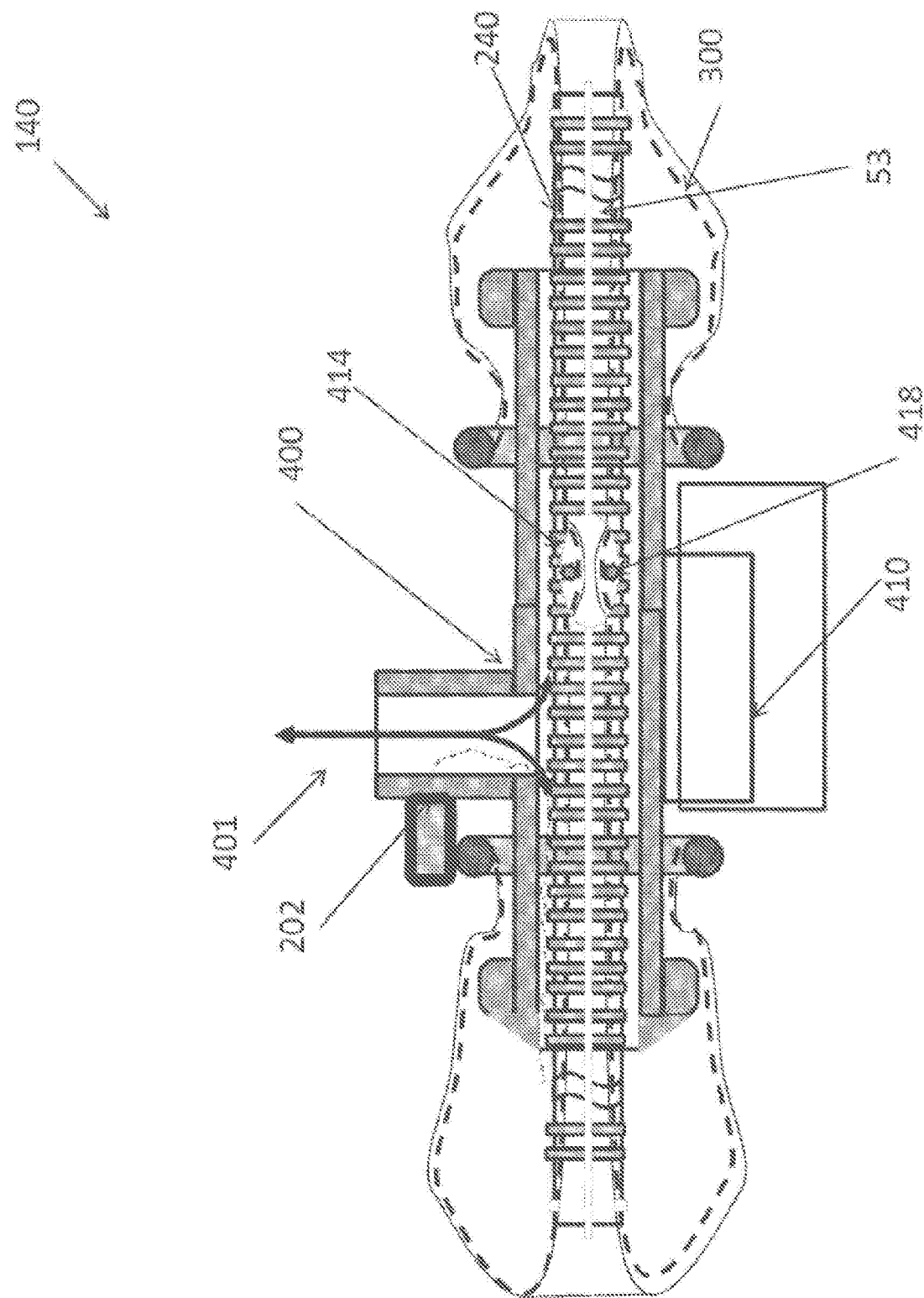
FIG. 14 is a schematic illustration of an embodiment of a single-valve endoscopic probe with flexible sleeve, constructed and operative in accordance with the invention, featuring a planetary advancing gear configured for operation in conjunction with the sleeve of FIG. 12 and/or with an optional internally serrated/indented sheath.

A sprocket wheel or another toothed or friction based mechanism (Examples are illustrated in FIGS. 13-14) can engage sheath 230 (or 220), and thereby force movement of sheath 230, back and forth, to effect insertion or retraction of sheath 230 into or out of colon 101, respectively. It is noted that sprockets 416 engage the external face of sheath 230 within bore 52 of valve unit 401 (or valve unit 40) where sheath 230 is not covered by sleeve 30.

Figure 12:
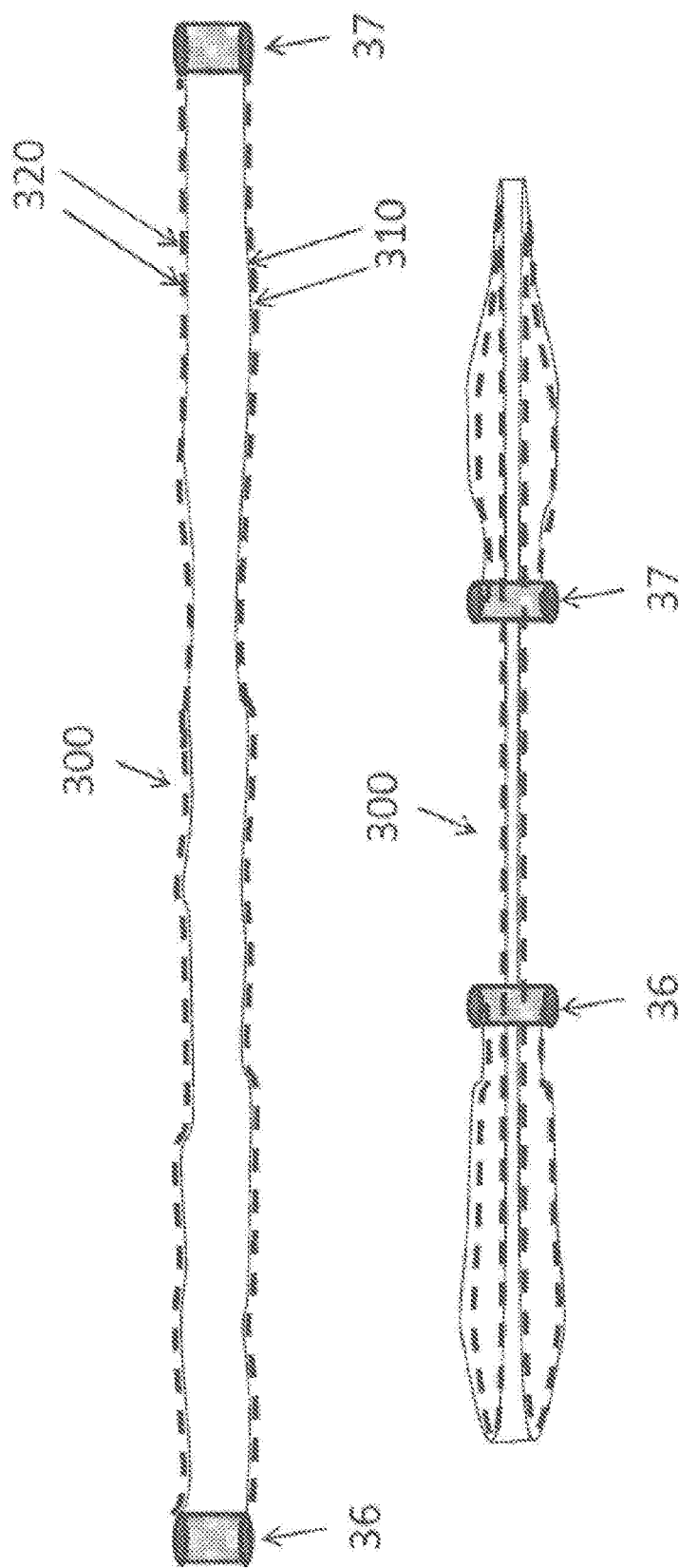
FIG. 12 includes schematic illustrations of an embodiment of an indented sleeve in extended and folded modes, constructed and operative in accordance with the invention, featuring indentations for facilitating advancing and centering of the sleeve.

An alternative configuration is shown in FIG. 12, which includes schematic illustrations of indented sleeve 300 in extended and folded modes, constructed and operative in accordance with the invention, featuring indentations 310 for facilitating advancing and centering of the sleeve. Indentations 310 can be external or internal circumferential notched recesses, grooves or depressions, separated by bulging protrusions 320, rendering the surface of indented sleeve 300 serrated or jagged, configured to engage a sprocket or a toothed propulsion mechanism that would force a pull of sleeve 300 toward the distal or proximal direction. Sheath 20 which is trapped within sleeve 300 would then be forced to advance or retreat, as sleeve 300 is forced to move toward the distal or proximal direction, respectively.

Further alternative configurations are shown in FIGS. 13-14. FIG. 13 is a schematic, cross-sectional illustration of an embodiment of single-valve endoscopic probe 130, constructed and operative in accordance with the invention, featuring an externally grooved sheath 230 and an advancing gear 413 (sleeve is not shown). The teeth of spur or sprocket 416 of planetary advancing gear 413 engage the externally grooved (or serrated, indented) surface of sheath 230, and thereby force movement of sheath 230, back or forth, to effect insertion or retraction of sheath 230 distal end wise or proximal end wise, respectively.

FIG. 14 is a schematic illustration of an embodiment of a single-valve endoscopic probe 140 with an optional flexible sleeve 300, an optional internally serrated/indented sheath 240, constructed and operative in accordance with the invention, featuring an advancing gear 414 configured for operation in conjunction with indented sleeve 300 of FIG. 12 and/or optional internally serrated/indented sheath 240. Spurs or sprocket wheels 418 are disposed within bore 53 of sheath 240. When sheath 240 is used, the teeth of sprocket 418 of advancing gear 414 engage the internally serrated/indented surface of sheath 240, and thereby force movement of sheath 240, back or forth, to effect insertion or retraction of sheath 230 distal end wise or proximal end wise, respectively. In addition or alternatively, sprocket 418 of advancing gear 414 is disposed between the internal face of sheath 240 (or sheath 20) the teeth of sprockets 418 engage the rugged surface of sleeve 300 that force a pull of sleeve 300 toward the distal or proximal direction. If sheath 20 is used, it is trapped within sleeve 300 and would then be forced to advance or retreat, as sleeve 300 is forced to move toward the distal or proximal direction, respectively. If sheath 240 is used the teeth of sprocket 418 of planetary advancing gear 414 engage the externally grooved surface of sheath 240 (in which case sleeve 30 is used or sleeve 300 is moved by a separate gear). An elongated central slit in sheath 240 (or sheath 20) provides for connecting wiring, or fora drive axle required to propel sprockets 418. Alternatively, advancing gear 414, which is isolated without wiring or mechanical connection to a propulsion conveying mechanism, can include electric motors mounted to sheath 20 that are induced to revolve by external electromagnetic fields, and pull sheath 240. Further optionally, the sleeve driving mechanism may be located outside sheath 240, inside valve unit 400, while engaging sleeve 300 through partially slotted sheath 240 or series of holes perforated along sheath 240 (similar to holes 210 of sheath 220 of FIG. 11) and matching the teeth steps of sprockets 418 and also accommodating the different translational movements of sheath 240 and sleeve 300.

Figure 15:
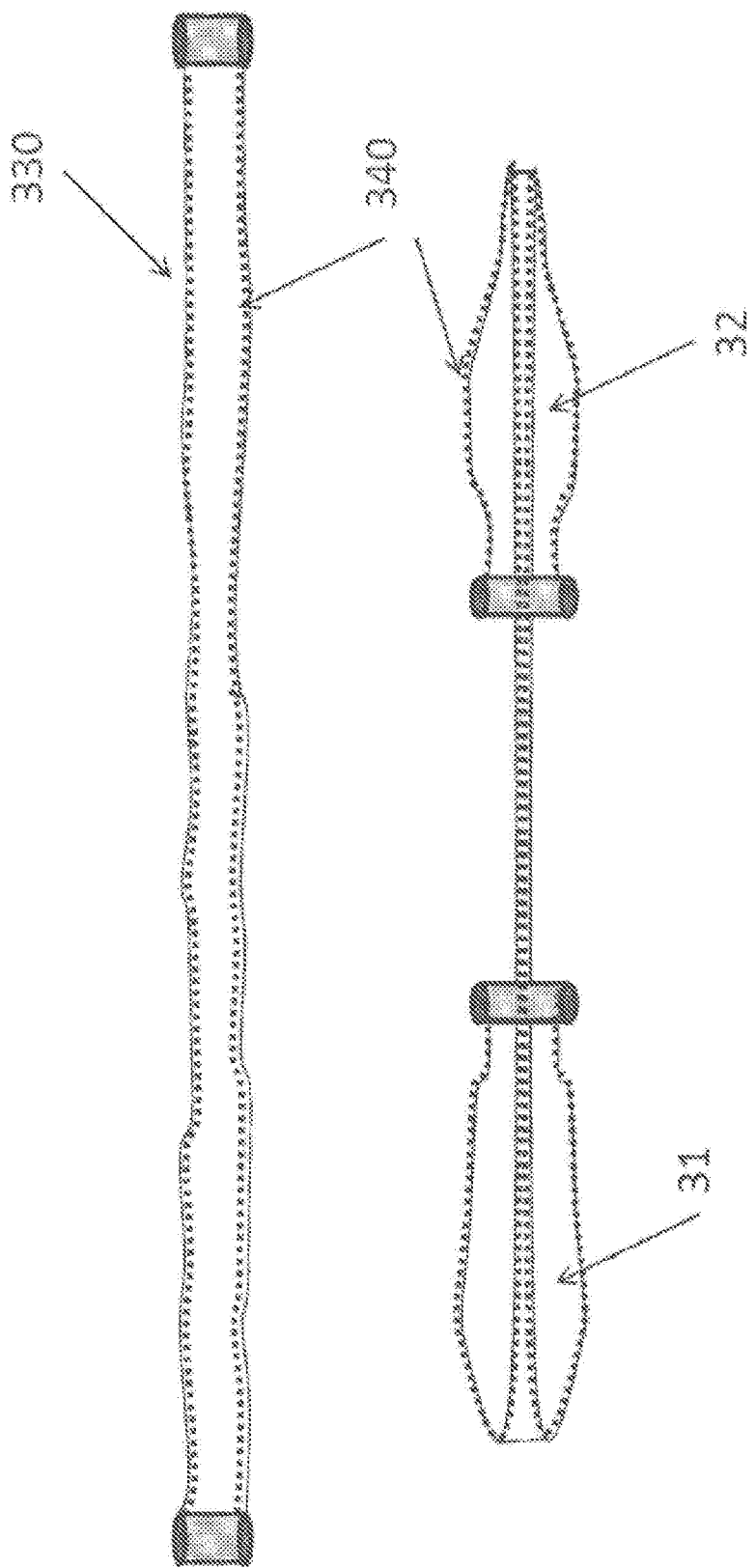
FIG. 15 is a schematic illustration of an embodiment of a sleeve in extended and folded modes, constructed and operative in accordance with the invention, featuring anesthetic/medical coating.

FIG. 15 is a schematic illustration of an embodiment of sleeve 330 in extended and folded modes, constructed and operative in accordance with the invention, featuring anesthetic deposit or coating, denoted 340. Anesthetic coating 340 overlays the internal face of sleeve 330. ('internal' when sleeve 300 is in an unfolded configuration as in the upper configuration of FIG. 15). When the proximal and distal portions 32 and 31 of sleeve 330 are folded inside out as shown in the bottom illustration of FIG. 15, to engage the configuration of covering sheath 20 and anchoring to valve unit 40, anesthetic coating 240 faces the external portion of probe 10 and thus is placed in direct contact with the internal wall of human colon 101, allowing release of anesthetic substances to the colon organs. The term 'anesthetic' or 'anesthetic/medical' refers to any and all medical substances, for effecting any medical treatment, soothing, lubricating or any other effect. Accordingly, despite its title, 'anesthetic' coating 340 is not limited to the inclusion of anesthetics, and may exclude anesthetics and/or other ingredients, such as markers that react to blood or any human body substance and may be used for indicating bleeding or bleeding location.

Figure 16:
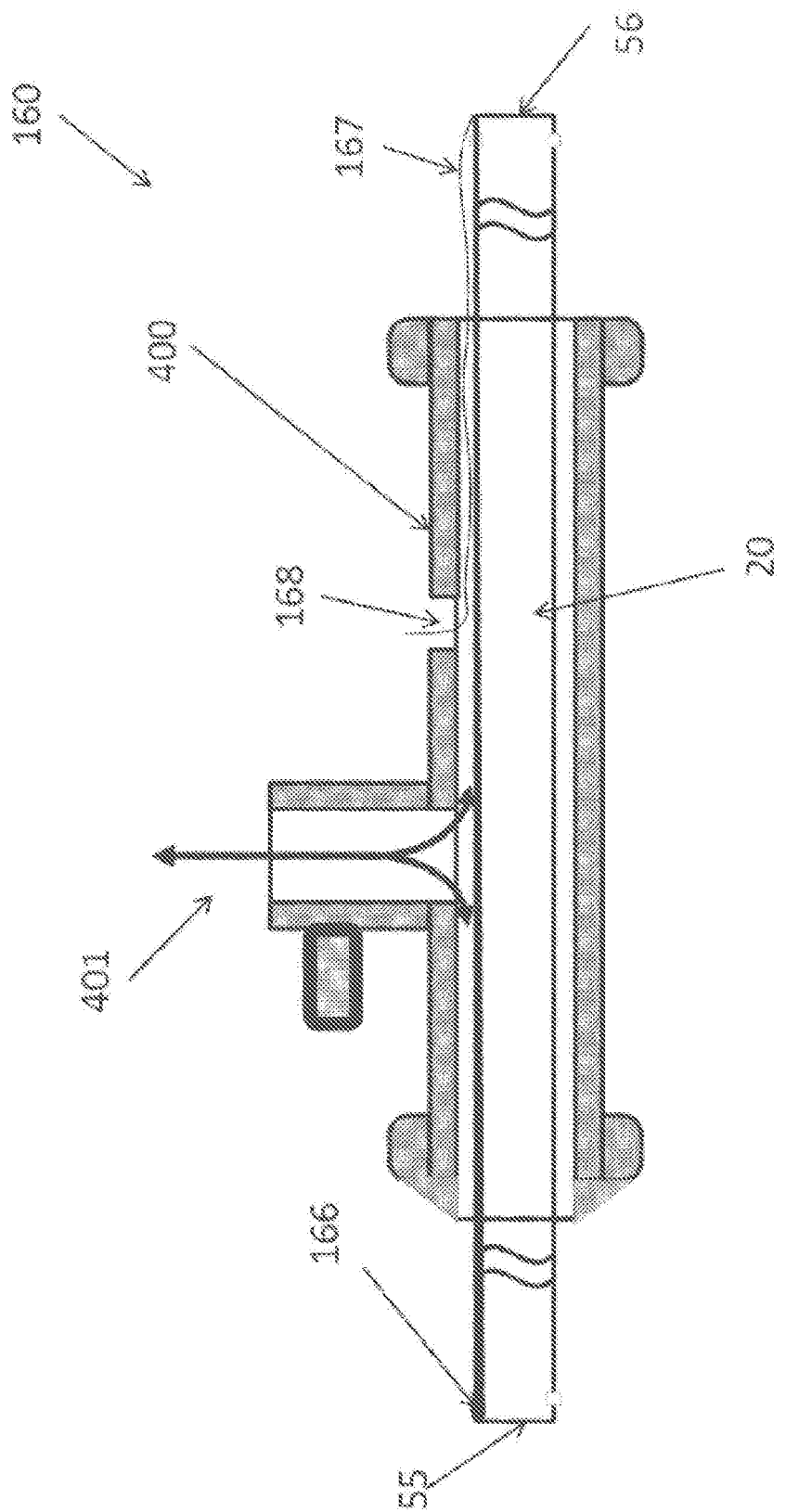
FIG. 16 is a schematic, cross-sectional illustration of an embodiment of a single-valve endoscopic probe, constructed and operative in accordance with the invention, featuring sheath-embedded camera.

FIG. 16 is a schematic, cross-sectional illustration of an embodiment of a single-valve endoscopic probe 160, constructed and operative in accordance with the invention, featuring sheath-embedded camera 166 (sleeve is not shown). Data and illumination wiring 167 is inserted through (hermetically sealed) aperture 168 valve unit 400 (or 40) and is further embedded along the entire length of the wall of sheath 20 from its proximal tip 56 to its distal tip 55. A camera 166 can include any known sensors as well as illumination, such as LED illumination, as well as treatment appliances which are not required to pierce sleeve 30.

Figure 17:
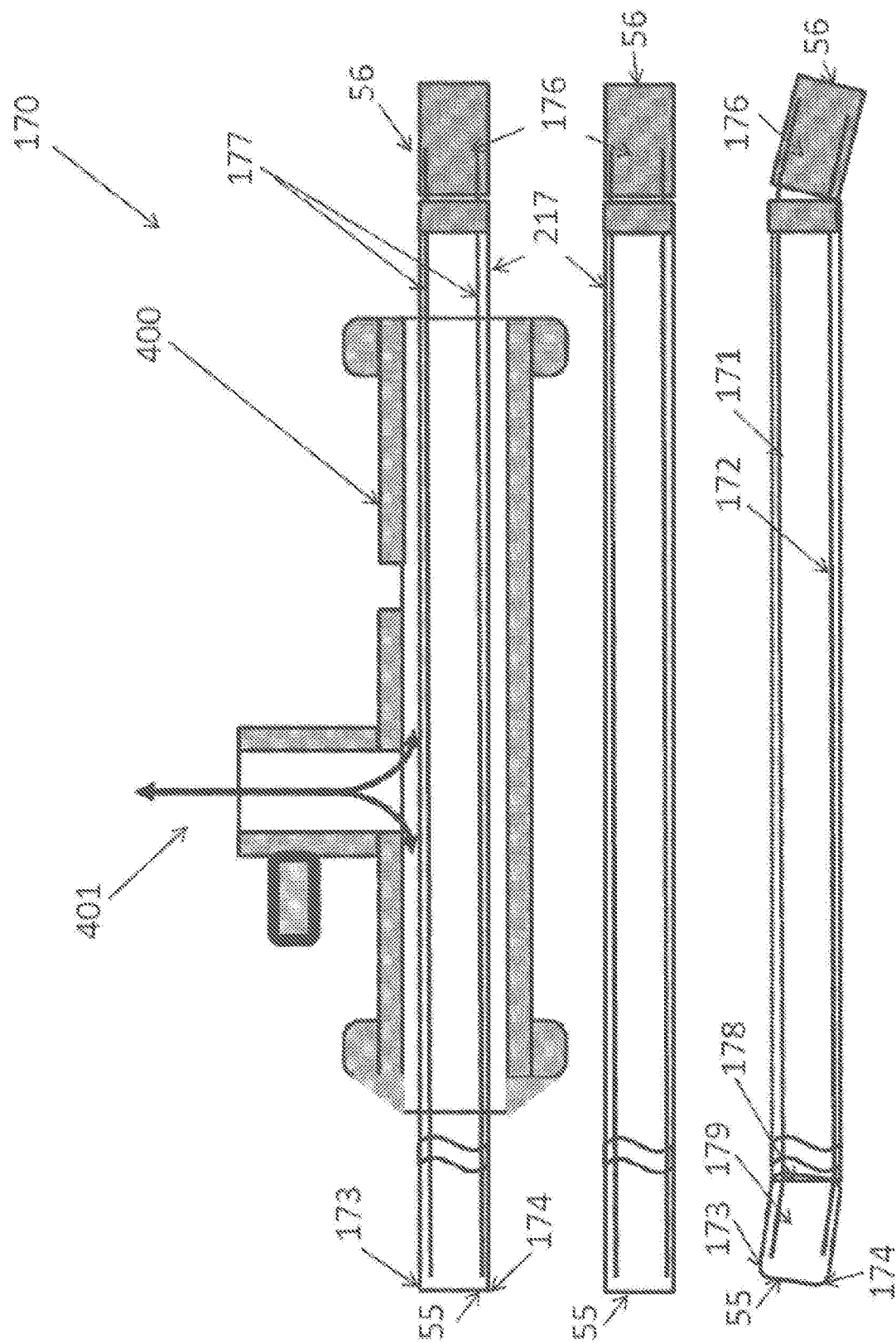
FIG. 17 includes schematic, cross-sectional illustrations of an embodiment of a single-valve endoscopic probe, constructed and operative in accordance with the invention, featuring sheath pulling wires for sheath tip angulation and steering.

FIG. 17 includes schematic, cross-sectional illustrations of an embodiment of a single-valve endoscopic probe 170, constructed and operative in accordance with the invention, featuring sheath pulling wires 177 for sheath tip angulation and steering (sleeve is not shown). A pair of oppositely disposed wires 177 is shown for demonstrating tip tilt angulation in a vertical axis. Alas, the rotation of sheath 217 for tip tilts in other axis may experience resistance when sheath 217 is warped with the windings of colon 101 and/or as the sleeve is inflated, accordingly further such pairs may be disposed along the internal circumference of sheath 20. Wires 177 are fixated to two opposed locations at distal tip 55. Wire 171 is connected at one end 173 of tip 55 and wire 172 is connected to the opposed end 174 of tip 55. A rigid portion 176 of sheath 217 is disposed at the proximal end 56 of sheath 217, and is separated therefrom, thereby allowing its tilting by the operator toward any of wires 171 or 172. When portion 176 is tilted toward wire 172, wire 171 is pulled and in turn pulls tip 55 at its end 173. Sheath 217 is allowed to bend near its tip, such as by flexible or weakened section 178 or a hinged connection at section 178, and therefore tip portion 179 tilts toward tip end 173 and angulates sheath 217, to meet the winding required to adapt the curls of colon 101.

Figure 18:
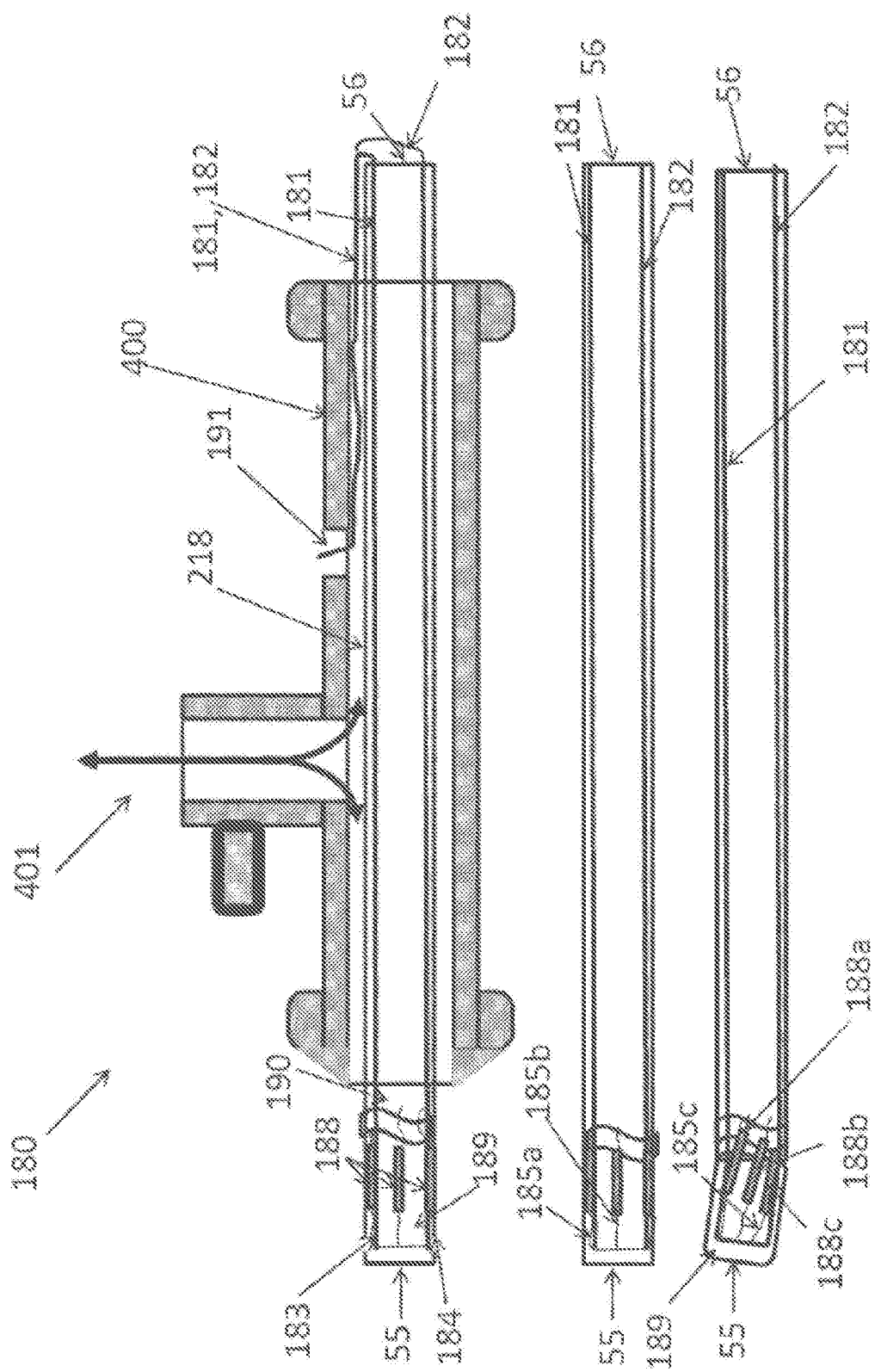
FIG. 18 includes schematic, cross-sectional illustrations of an embodiment of a single-valve endoscopic probe, constructed and operative in accordance with the invention, featuring sheath pulling wires with inchworm motors for sheath tip angulation and steering.

FIG. 18 includes schematic, sectional illustrations of an embodiment of a single-valve endoscopic probe 180, constructed and operative in accordance with the invention, featuring sheath pulling wires with inchworm motors 188 for sheath tip angulation and steering. Probe 180, includes sheath 218 and wires 181 and 182 which feed power and control to inchworm motors 188 and are disposed within sheath 218, and are curling about sheath proximal end 56 and (hermetically sealed) aperture 191 disposed in valve unit 400. Other types of motors or actuators may be applied instead of inchworm motors 188.

Wires 185a, 185b, 185c are disposed at distal tip 55, about tiltable tip portion 189, similar to the embodiment of FIG. 17. Inchworm motors 188a, 188b, and 188c, which are fixated to the sheath tip portion 190, grip wires 185a, 185b, 185c, respectively. Electrical supply (and control) wiring can extend along with wires 181, 182 or embedded within and along the wall of sheath 218. Activation of inchworm motor 188a pulls wire 185a and forces tip portion 189 to tilt upwards, toward motor 188a. Activation of both inchworm motors 188c and 188b pulls wires 185b and 185c and forces tip portion 189 to tilt toward motors 188c and 188b.

Figure 19:
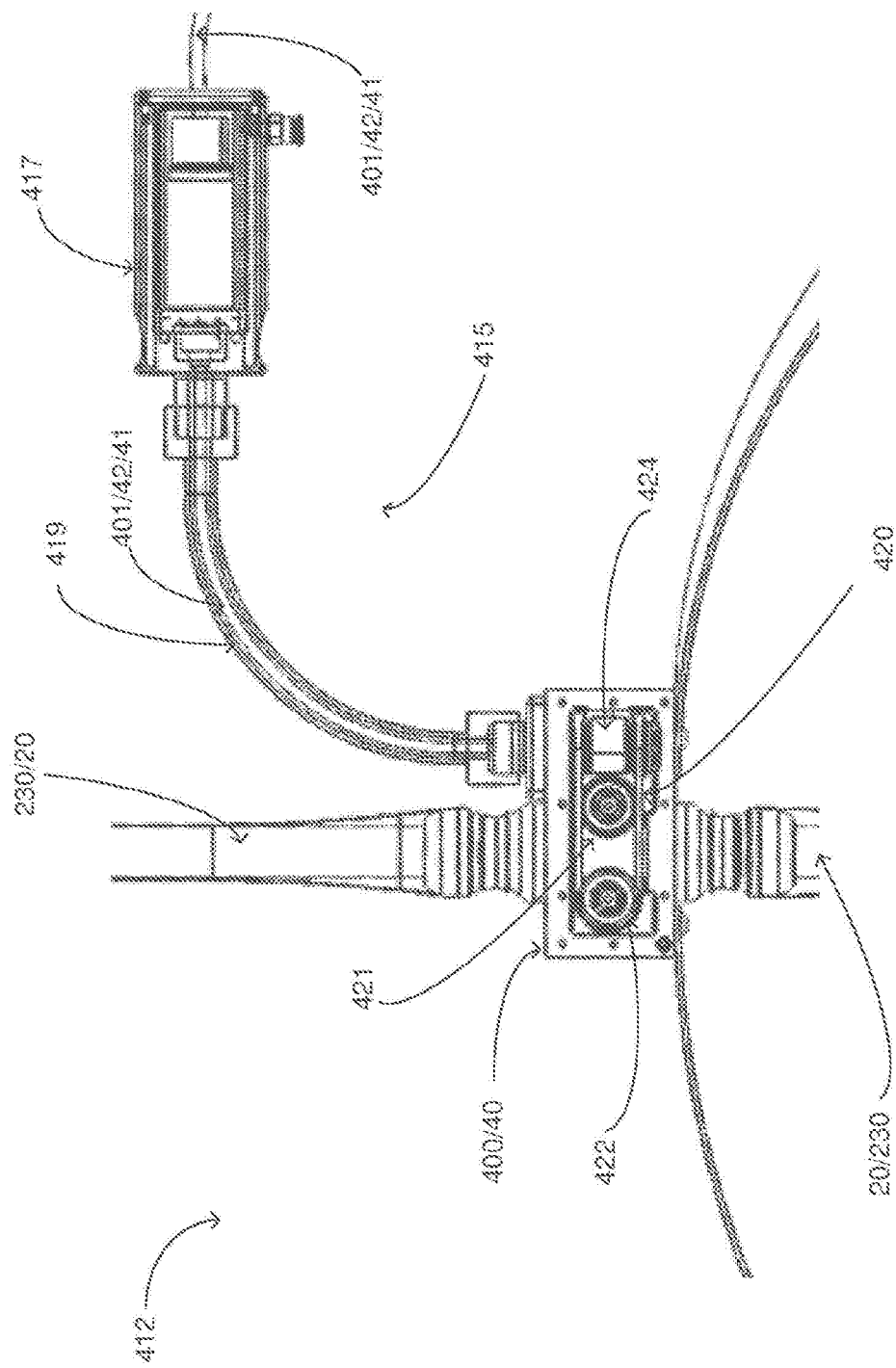
FIG. 19 is a schematic, cross-sectional illustration of an embodiment of a valve unit incorporating a drive mechanism for propelling an endoscopic probe, constructed and operative in accordance with the invention.
Figure 20:
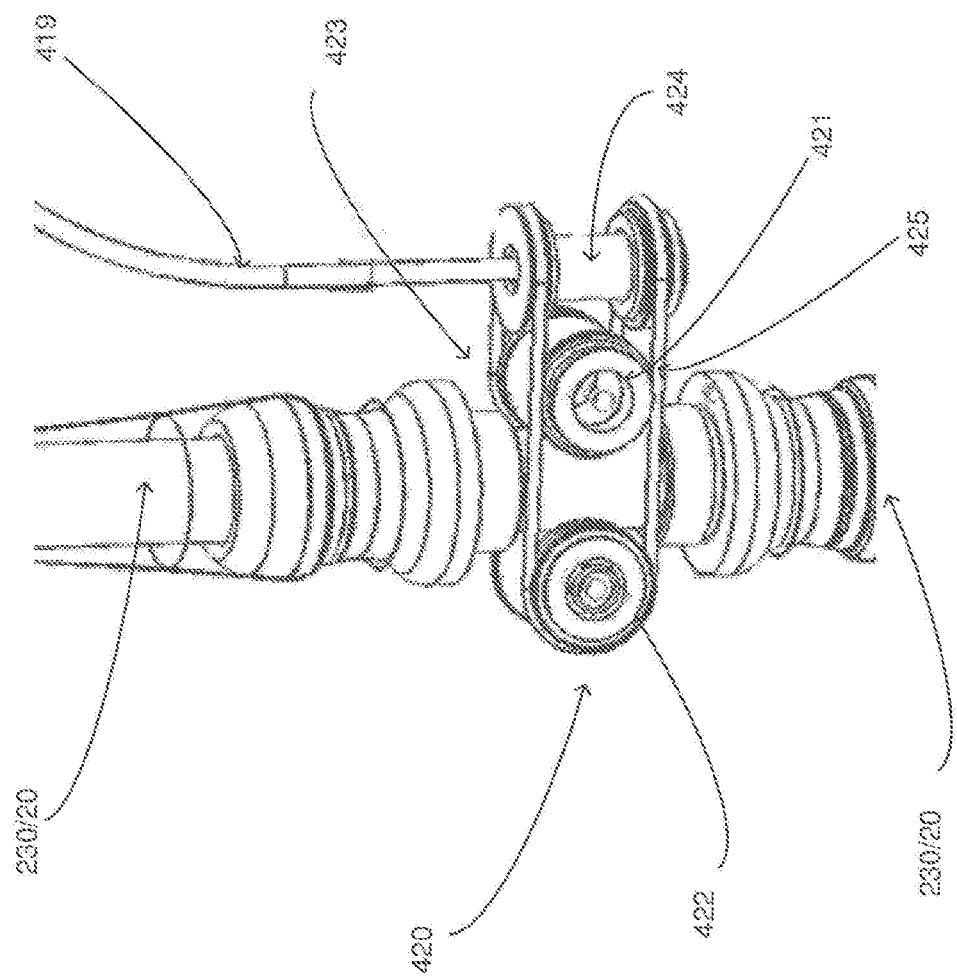
FIG. 20 is a schematic illustration of the torque splitter of the drive mechanism of FIG. 19.
Figure 21:
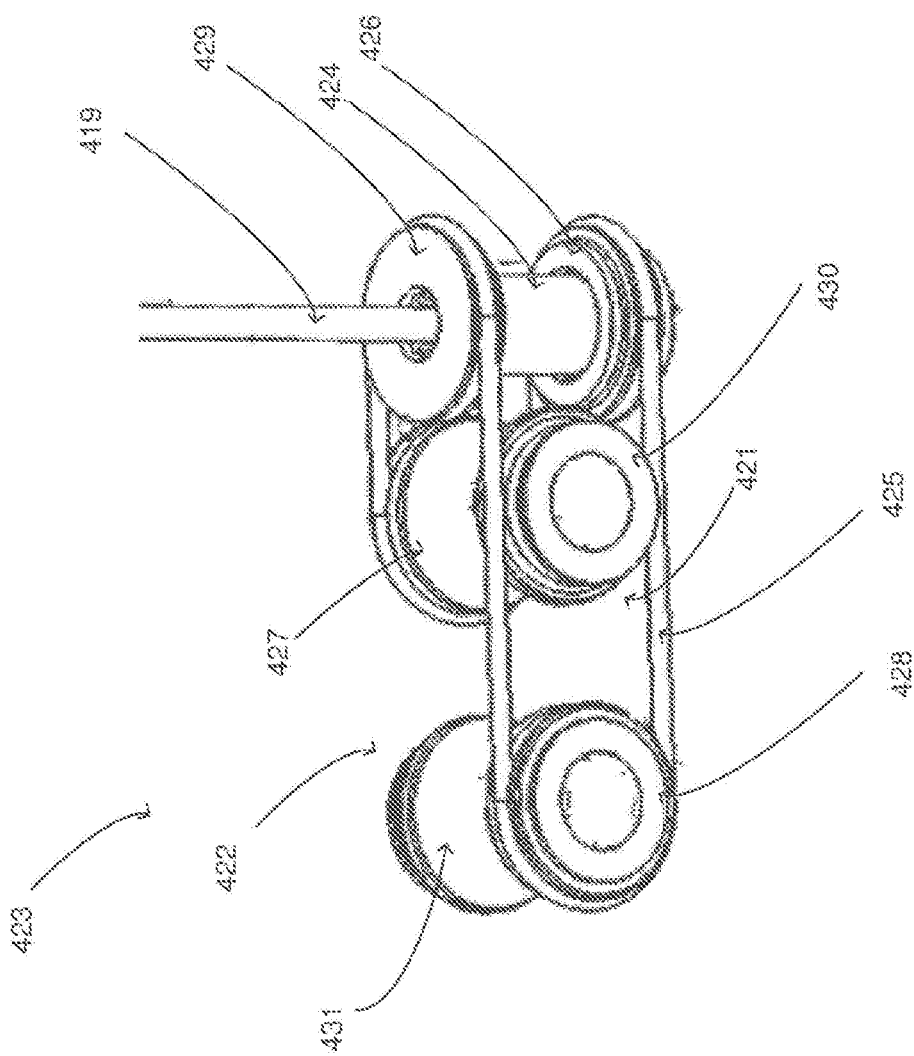
FIG. 21 is an enlargement of the compound pulley system of the torque splitter of FIG. 20.

FIG. 19 is a schematic, cross-sectional illustration of an embodiment of a valve unit 412 incorporating drive mechanism 415 for propelling an endoscopic probe, constructed and operative in accordance with the invention. Drive mechanism 415 is an example of a propulsion mechanism that can be applied for advancing gear 413 of FIG. 13, or adapted to advancing gear 414 of FIG. 14. Drive mechanism 415 is combined with components of valve unit 40 or 400. Drive mechanism 415 includes electrical motor unit 417, flexible drive shaft spindle 419, and torque splitter 420. Reference is now also made to FIGS. 20 and 21. FIG. 20 is a schematic illustration of torque splitter 420 of drive mechanism 415 of FIG. 19. FIG. 21 is an enlargement of compound pulley system 423 of torque splitter 420 of FIG. 20. Drive mechanism 415 further includes two output drive drums 421 and 422 that can operate, similar to sprockets 416 of FIG. 13, to advance or retract sheath 20 (or sheath 230) which is held between drums 421 and 422. A valve pipe designated 401/42/41, such as of valve 41, 42 or 401, enters valve unit 40 or 401 through flexible drive shaft spindle 419, and motor unit 417, wherein both—flexible drive shaft spindle 419, and motor unit 417 incorporate a passage therein to accommodate pipe 401/42/41 into valve unit 40 or 400. Flexible drive shaft spindle 419 can be formed as hollow shaft internally accommodating pipe 401/42/41. Alternatively, pipe 401/42/41 includes in internal pipe accommodating flexible drive shaft spindle 419. Electrical motor unit 417 turns flexible drive shaft spindle 419, which turns the two output drive shafts 421 and 422, via torque splitter 420, which is mounted inside valve unit 40 or 400, and embrace sheath 20 or 230 for its propulsion. Drive drums 424 and 426 are set up to furnish revolutions in two opposed rotational directions. Sheath 20 or 230 is held between drums 421 and 422 which roll along the longitudinal external sides of sheath 20 or 230 and thereby transfer their rotational movement into a linear movement of sheath 20 or 230, resembling sprocket wheels 416 of FIGS. 13. Torque splitter 417 can incorporate any splitting mechanism, including differential, planetary, having spur gear trains, and the like. An example of one such splitting mechanism is compound pulley system 423. Torque splitter 417 includes input drum 424, two output drums 421 and 422, and endless taut cable or belt 425. Input drum 424 is connected to, and thereby rotated by, flexible drive shaft spindle 419, which conveys the rotational torque of electrical motor unit 417 to input drum 424. Input drum 424 is coupled with output drums 421 and 422 via endless belt 425, which serpentines to convey the torque from input drum 424 to output drums 421 and 422. Input drum 424 incorporates grooved input pulley 426. Output drum 421 features grooved output pulley 427 and output drum 422 features grooved output pulley 428. A freely rotatable sheave pulley 429 is also disposed about drum 424 or coupled therewith, such as by ball bearing that isolates sheave pulley 429 from the rotations of drum 424. Endless belt 425 is wound about an arc of contact of each of pulleys 426, 427, 428, and 429 in circumferential grooves laterally disposed in the rim of pulleys 426, 427, 428 and 429, providing the adequate friction with belt 425, such that the driving force applied by pulley 426, drives belt 425, and belt 428 drives pulleys 427 and 428. If required, toothed interface is provided to belt 425, and pulleys 426, 427, and 428 to increase the bilateral grip between belt 425 and each of pulleys 426, 427, and 428. However, sheave pulley 429 is provided only as a looped around pulley without transfer of force. Endless belt 425 is looped around pulleys 427 and 428, which are disposed toward opposite directions and runs along two parallel paths between pulleys 427 and 428, both paths curling about pulleys 426, 429, thereby, belt 425 rotates pulleys 427 and 428 in the opposite rotational direction. Pulleys 427 and 428 are connected to drums 421 and 422, respectively. Each of drums 421, 422, may now be coupled with sheath 20 or 230, directly or through any adequate engaging or coupling arrangement, such as wheels 430, 431, which are connected to drums 421, 422, respectively, and which can be sprocket wheels, similar to sprockets 416 or 418.

Figure 22:
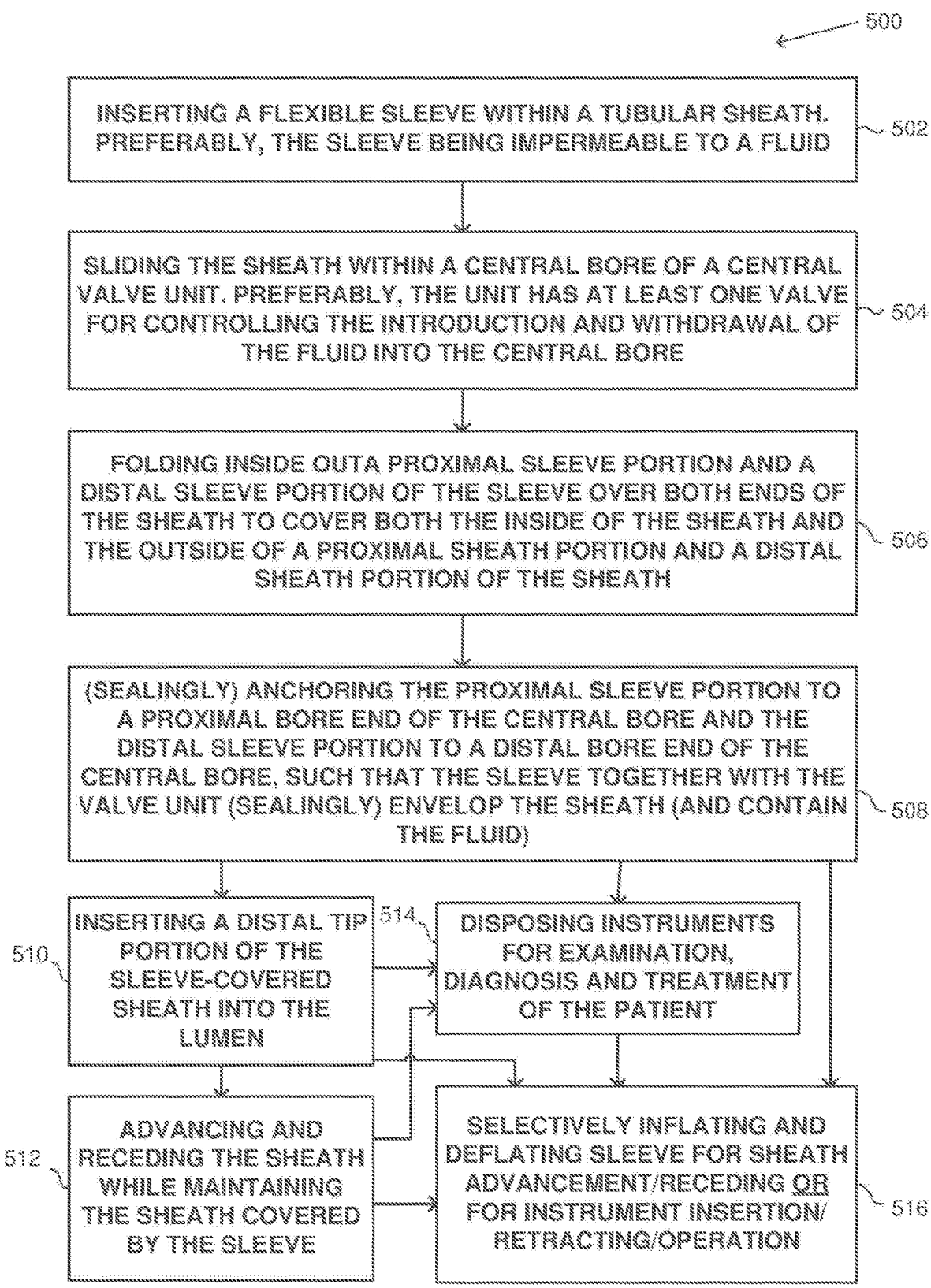
FIG. 22 is a block diagram of a method for propelling an endoscopic probe within a lumen, operative in accordance with an embodiment of the disclosed invention.

Reference is now made to FIG. 22, which is a block diagram of a method 500 for propelling an endoscopic probe within a lumen, operative in accordance with an embodiment of the disclosed invention.

In procedure 502, a flexible sleeve is inserted within a tubular sheath. With reference to FIGS. 1-5, sleeve 30 is inserted within sheath 30. Preferably, the sleeve is impermeable to a fluid. The fluid may be gas, pressurized gas, or liquid. Optionally, a portion of the sleeve includes a variable diameter to accommodate variable lumen, such as sleeve 35 of FIG. 6. Further optionally, a face of the sleeve is coated/deposited with an anesthetic or other medical substance, such as sleeve 330 of FIG. 15.

In procedure 504, the sheath is slid through a central bore of a central valve unit, such as sheath 20 which is slid through bore 52 in FIGS. 1-5. Preferably, the central valve unit includes at least one valve for controlling the introduction and withdrawal of the fluid into the central bore. In reference to FIGS. 1-5 and 7, central valve unit 40 includes two valves, 41, 42, while central valve unit 400 in FIGS. 10, 11, 13, 14, and 16-18, includes a single valve 401.

In procedure 506, a proximal sleeve portion, and a distal sleeve portion of said sleeve are folded inside out over both ends of the sheath to cover both the inside of the sheath and the outside of a proximal sheath portion and a distal sheath portion of the sheath. In reference to FIGS. 1-5, proximal sleeve portion 32, and distal sleeve portion 31 of sleeve 30 are folded inside out over both ends 55, 56 of sheath 20 to cover both the inside face internal bore 53 of sheath 20 and the outside of proximal sheath portion 22 and distal sheath portion 21 of sheath 20.

In procedure 508, the proximal sleeve portion is anchored to a proximal bore end of the central bore the distal sleeve portion is anchored to a distal bore end of the central bore, such that the sleeve together with the valve unit envelop the sheath. Preferably, the proximal sleeve portion is sealingly anchored to the proximal bore end of the central bore, and the distal sleeve portion is sealingly anchored to the distal bore end of the central bore, such that the sleeve together with the valve unit sealingly contain the fluid, while the sleeve is impermeable to the fluid (as mentioned in procedure 502) and while the central valve unit includes at least one valve for controlling the introduction and withdrawal of the fluid into the central bore (as mentioned in procedure 504). In reference to FIGS. 1-5, proximal sleeve portion 31 is sealingly anchored to proximal bore end of central bore 52 at anchoring 23, distal sleeve portion 32 is sealingly anchored to distal bore end 50 of central bore 52 at anchoring 23, such that sleeve 30 together with valve unit 40 envelop sheath 20.

In procedure 510, a distal tip portion of the sleeve-covered sheath is inserted into the lumen, similar to the configuration of probe 10 in FIG. 1, for initiating the insertion of distal portion 21 of sheath 20 into lumen 101, as shown in FIGS. 2-5.

In procedure 512, the sheath is advanced and retracted, as required to serve the medical procedure, while maintaining the sheath covered by the sleeve, as is shown in several configurations in FIGS. 1-5.

The above procedures provide for the effective operation of method 500 for propelling an endoscopic probe within a lumen. It is noted that the method is primarily intended to be applied with a fluid, namely such that the sleeve together with the valve unit sealingly contain the fluid (procedure 508). To that preferable end, the central valve unit includes at least one valve for controlling the introduction and withdrawal of a fluid into said central bore (procedure 504), the sleeve is impermeable to the fluid (procedure 502), and the anchoring comprises sealingly anchoring the proximal sleeve portion to a proximal bore end of the central bore and the distal sleeve portion to a distal bore end of the central bore, such that the sleeve together with the valve unit sealingly envelop the sheath (procedure 508).

In procedure 514, instruments for examination, diagnosis and treatment of the patient are disposed in at least one of: within the central bore of the sheath outside the sleeve, within the central bore of the sheath within the sleeve, when inserted between the sheath and the sleeve, embedded in the sheath, deployed beside the sheath within the sleeve, and deployed beside said sheath outside said sleeve. In reference to FIG. 5, the wiring of instrument 80 is disposed within central bore 53 of sheath 20 outside sleeve 30. In FIG. 9, instrument 80 is combined in rod 47 which is disposed within central bore 53 of sheath 20 outside sleeve 30. In FIGS. 7, 10, 11, 13, 14, forward illumination 202, including wiring, is inserted between sheath 20 and bore 52 within the sleeve for facilitating inspection around distal edge 55 of distal portion 21 of sheath 20 when inserted within colon 101 of human body 100, and camera 166 is embedded in sheath 30 as exemplified in FIG. 16. Procedure 514 is performed before procedure 502 or in parallel to any of procedures 504-508, corresponding the desired location of the instrument with regard to the central bore, the sheath and the sleeve.

In procedure 516, the sleeve, or a portion thereof, is selectively inflated or deflated for sheath advancement/receding or for instrument insertion/retracting/operation. Procedure 516 may be performed after procedures 508, 510, 512, or 514, or in lieu of, or simultaneously with, procedures 510, 512, or 514. As noted above with reference to FIG. 5, deflation of sleeve 30 may involve complete extraction of fluid therefrom to the extent sleeve 30 is tightly adhered by the internal vacuum created within sleeve 30 to both sides of sheath 20, rendering both into an overtube-like configuration, leaving clear and wide passage within bore 53 for convenient insertions and retractions of diagnostic tools and instruments. When the sleeve is inflated and is advanced or retracted in conjunction with, or for the sake of, advancing or receding the sheath within colon 101, the portion of the sleeve disposed within the bore of the sheath advances/retracts twice the length the sheath advances/recedes, while typically grasping and carrying the inserted tool/instrument. Accordingly, the sleeve can be deflated, intermittently—if required, for allowing an offsetting reverse push or pull of the inserted object within bore 53, and thereby to compensate over-progression. The sheath may be perforated for easy passage of fluid within the sleeve, allowing fast inflating and deflating of the sleeve. In reference to FIG. 11, sheath 220, allows easy passage of fluid, liquid or gas, and for fast inflating and deflating of the sleeve.

Figure 23:
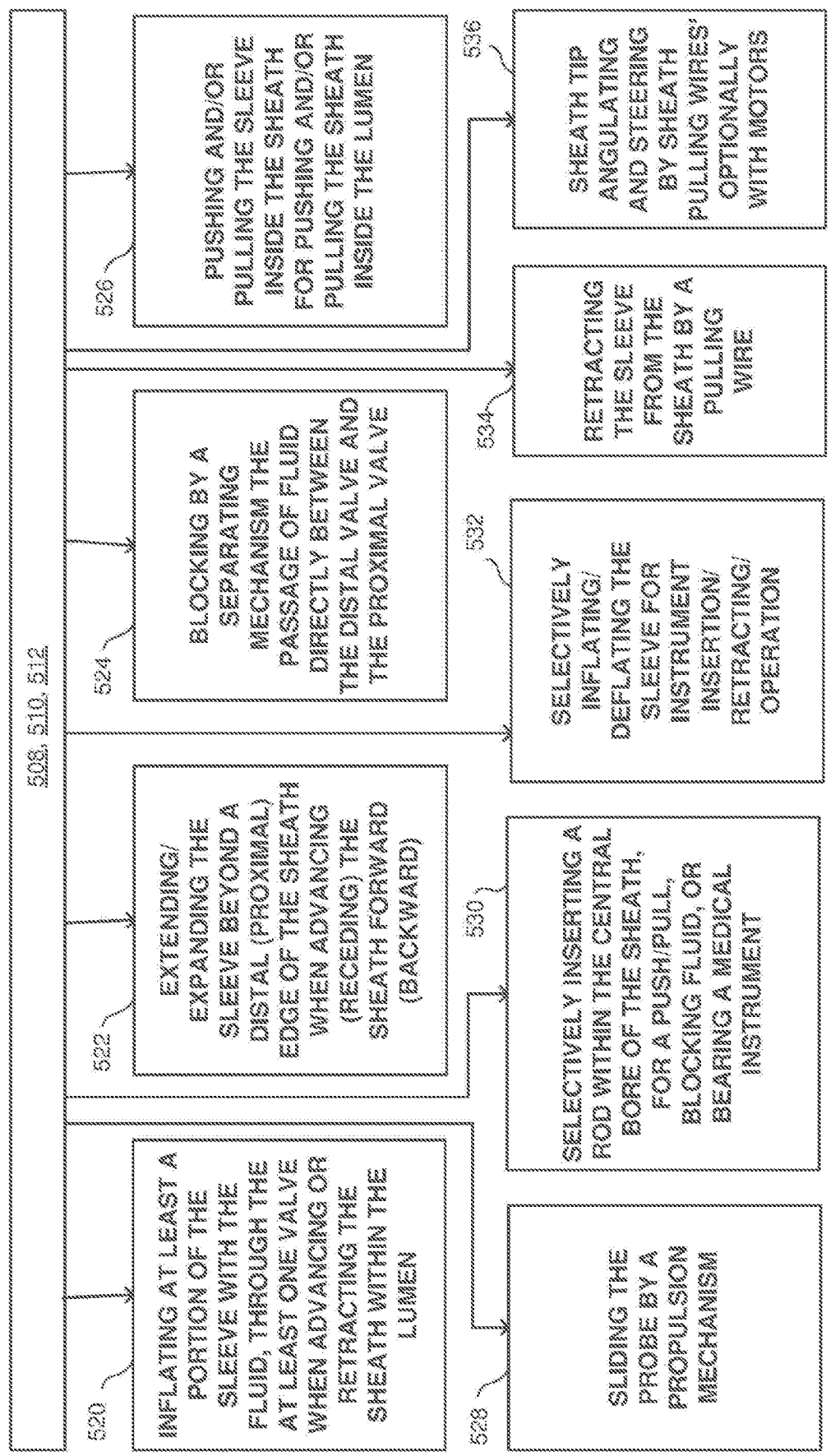
FIG. 23 is a block diagram of sub-procedures of procedure 520 of the embodiment of FIG. 22.

Method 500 may include further optional or preferable procedures and features outline below. Reference is now made to FIG. 23 which is a block diagram of sub-routines or sub-procedures of procedure 516 of the embodiment of FIG. 22. Accordingly, procedure 516 may further include any of sub-procedures 520-536.

In sub-procedure 520, at least a portion of the sleeve is inflated with the fluid, through the at least one valve, when advancing or retracting the sheath within the lumen. Preferably, a distal side of the sleeve is inflated to insert the probe (while the proximal side of the sleeve may be allowed to deflate, or actively deflated), and a proximal side of the sleeve is inflated to extract the probe (while the distal side of the sleeve may be allowed to deflate, or actively deflated), using the central valve unit. In reference to FIGS. 1-5, distal side 31 or pocket 33 of sleeve 30 is inflated to insert probe 10 (while proximal side 32 or pocket 34 of sleeve 30 may be allowed to deflate, or is actively deflated), and proximal side 32 of sleeve 30 is inflated to extract probe 10 (while distal side 31 or pocket 33 of sleeve 30 may be allowed to deflate, or is actively deflated), using central valve unit 40.

In sub-procedure 522, the sleeve is extended/expanded beyond a distal edge of the sheath when advancing the sheath forwards, or beyond a proximal edge of the sheath when receding the sheath backwards. Preferably, the at least one valve mentioned in procedure 504 includes a distal valve and a proximal valve. The sleeve is extended/expanded beyond a distal edge of the sheath, as fluid is introducing into a distal portion of the sheath through the distal valve and the sheath advances forward. The sleeve is extended/expanded beyond a proximal edge of the sheath, as fluid is introduced into a proximal portion of the sheath through the proximal valve and the sheath advances backward. In reference to FIGS. 1-5, sleeve 30 is extended/expanded beyond distal edge 55 of sheath 20, as fluid is introducing into distal portion 21 of sheath 20 through distal valve 41 and sheath 20 advances forward. Sleeve 30 is extended/expanded beyond proximal edge 56 of sheath 20, as fluid is introduced into proximal portion 22 of sheath through proximal valve 42 and sheath 20 advances backward.

In sub-procedure 524, the passage of fluid directly between the distal valve and the proximal valve is blocked by a separating mechanism. In reference to FIGS. 1-5 and 7, O-ring 43, as well as head 48 of rod 45 in FIG. 4, and optional separating mechanism 44 in FIG. 1, block passage of fluid directly and between distal valve 41 and proximal valve 42.

In sub-procedure 526, the sleeve is pushed and/or pulled inside the sheath for pushing and/or pulling the sheath inside the lumen. In reference to FIG. 4, head 48 of rod 45 pushes and/or pulls sleeve 30 inside sheath 20 for pushing and/or pulling sheath 20 inside lumen 101. In FIG. 14, mechanism 411 pushes and/or pulls sleeve 300 inside sheath 240 for pushing and/or pulling sheath 24 inside the lumen.

In sub-procedure 528, which may optionally be performed as a sub-procedure of procedure 504 and/or procedure 502, the probe is slid by a propulsion mechanism. The mechanism may include a sprocket wheel, a toothed mechanism, a friction based mechanism, an indented sleeve, a perforated sheath, a slotted sheath, an externally serrated/indented sheath, and/or an internally serrated/indented sheath. In reference to FIGS. 11-14, the probe is slid by propulsion mechanisms 411, 414, featuring sprocket wheels 416, 418 which are part of toothed mechanisms 411, 414, which are also examples of friction based mechanisms, indented sleeve 300 of FIG. 12, a perforated sheath as of FIG. 11, and slotted sheath or externally or internally serrated/indented sheath as of FIGS. 13 and 14.

In sub-procedure 530, which may optionally be performed as a sub-procedure of procedure 504 and/or procedure 502, a rod is selectively inserted within the central bore of the sheath, wherein the rod includes at least one of: a bulbous head for facilitating push/pull of the sheath, an expandable head for facilitating push/pull of the sheath, an expandable head for selectively blocking fluid flow inside the sleeve at a blocking location disposed within the bore of the sheath, and an instrument for examination, diagnosis and treatment of the patient. In reference to FIGS. 4 and 9, rod 45 is selectively inserted within central bore 53 of sheath 20, wherein the rod may incorporate a bulbous head 48 for facilitating push/pull of sheath 20, an expandable head 49 of rod 46 for facilitating push/pull of sheath 20 and/or for selectively blocking fluid flow inside sleeve 30 at a blocking location disposed within bore 53 of sheath 20, or instrument 80 for examination, diagnosis and treatment of the patient.

In sub-procedure 532 the sleeve is selectively Inflated and deflated for instrument insertion/retracting/operation. Deflation of the sleeve may involve complete extraction of fluid therefrom to the extent the sleeve is tightly adhered by the internal vacuum created within the sleeve to both sides of the sheath, rendering both into an overtube-like configuration (sleeve-"coated" sheath). Such a configuration leaves the widest possible clear passage within the bore of the sheath for convenient insertions and retractions of diagnostic tools and instruments, such as used, for instance, in polyp removal surgery.

As is noted with reference procedure 516 and elaborated with reference to FIG. 5, when sleeve 30 is inflated and is advanced or retracted in conjunction with, or for the sake of, advancing or receding the sheath within colon 101, according to procedure 520 or procedure 522, the portion of the sleeve disposed within the bore of the sheath advances/retracts twice the length sheath advances/recedes, and is typically clenched inwardly about the central axis of the bore. As a result, any object inserted through the sleeve, such as tool 80 in FIG. 5 (particularly its cable or rod) or rod 45 in FIG. 4, is firmly grasped by the inflated, inwardly clenching, sleeve which typically grasps and carries the inserted object twice the length by which the sheath progresses (to either direction). Accordingly, to avoid over-progression of the inserted object, the sleeve can be deflated, intermittently—if required, for allowing an offsetting reverse push or pull of the inserted object within the bore of the sheath, compensating for its already-occurred or prospective over-progression.

In sub-procedure 534, the sleeve is retracted from the sheath by a pulling wire, such as wire 38 in FIG. 8. This may also serve for the entire removal of the disposable sleeve, after the medical procedure is completed, allowing the insertion of a new sleeve for the next medical procedure.

In sub-procedure 536, the sheath tip is angulated and/or steered by sheath pulling wires. Optionally, the wires may be pulled by motors, such as inchworm motors. With reference to FIG. 17, sheath tip 179 is angulated and/or steered by sheath pulling wires 177, 171, 172. In reference to FIG. 18, wires 185a, 185b, 185c, may be pulled by motors 188, such as inchworm motors 188a, 188b, 188c.

Reference is now made to FIGS. 24A-28, concerning an endoscope adapter, which facilitates operation of the probe and an endoscope. FIGS. 24A and 24B are a schematic cross-sectional illustration and a schematic isometric illustration, respectively, of an embodiment of an endoscope adapter, denoted as adapter 600, constructed and operative in accordance with the invention. FIGS. 25A and 25B are a schematic cross-sectional illustration and a schematic isometric illustration, respectively, of endoscope adapter 600 of FIGS. 24A and 24B, when mounted on sleeve-covered-sheath 20 and conveying endoscope 81 there through.

Hollow probe 10 of FIGS. 1-5 enables insertion and accommodation of endoscopic and other instruments, herein denoted as endoscope 81, through tubular sheath 20 which is covered by sleeve 30. As noted above, that the term "endoscope", such as of endoscope 81, is used herein for short, and is not specifically limited to an endoscope or an endoscopic tool, and may refer to any instrument, for treatment, diagnosis or other purposes, that is used in the context of insertion and accommodation through sheath 20.

Endoscope adapter 600 is mountable to proximal end 22 of sleeve-covered-sheath 20. Endoscope adapter 600 allows insertion of endoscope 81 there through, into sleeve-covered-sheath 20.

Endoscope adapter 600 features adapter housing 604 which is sealingly (and preferably releasably) mounted to proximal end 22 of sleeve-covered-sheath 20.

Body fluids that usually pass through sleeve-covered-sheath 20 may leak or escape through gaps between endoscope adapter 600 and sleeve-covered-sheath 20, or between endoscope adapter 600 and endoscope 81. Such 'body fluids' are not limited to fluids or natural body-materials, and may include liquid (and non-liquid) faecal particles, blood, urine, as well as treatment liquids, washing liquids, and the like, which are often disposed for example in the intestine. To this end (of avoiding body-fluids leakage), endoscope adapter 600 includes at least one gasket for sealing at least one gap of the above-mentioned gaps, for withholding body fluids from escaping through the at least one gap. For example, housing-endoscope sealing gasket (O-ring) 606 seals the gap between adapter housing proximal side 631 and endoscope 81; and housing-sheath sealing gasket (O-ring) 608 seals the gap between adapter housing distal side 630 and sleeve-covered-sheath 20. Gaskets 606 and 608 provide the required sealing against leakage of body fluids. Body fluids penetrate in the direction denoted by perforated arrows 610 in FIG. 25A and accumulate in cavity 612 which is confined between endoscope adapter 600 (namely, within adapter housing 604), endoscope 81 and sleeve-covered-sheath 20. According to an alternative embodiment (wherein housing 604 is not necessarily applied), blocking leakage of such body fluid may be provided by a gasket such as sealing ring 652, which directly seals gap 602 between endoscope 81 and sleeve-covered-sheath 20.

In order to neatly and safely dispose of these body fluids, endoscope adapter 600 may include body fluids removal port, such as port 614, for allowing removal, preferably by suction (e.g., by an adequate pump which is coupled to port 614), of body fluids disposed in the cavity 612, which would flow in the direction denoted by perforated arrow 616 in FIG. 25A Endoscope adapter 600 may further include a clutch for selectively clasping sheath sleeve—30 in order to provide a support for sheath-covered-sleeve 20, while pushing or pulling endoscope 81. When sleeve 30 is inflated at the clutching area, the clutch clasps sleeve 30 and thereby supports sheath 20, which is distanced from sleeve 30 by the buffer of pressurized fluid therein. When sleeve 30 is deflated at the clutching area (or when the inner pressure within sleeve 30 is not sufficient to keep sheath 20 distanced from sleeve 20 under the clasping pressure of the clutch), the clutch may directly clasp sheath 20 through the thin segregation of sleeve 30, without the buffering of the fluid within sleeve 30. Such a clutch may feature a piston-clutch or any equivalent mechanism. Exemplary clutch 618 includes piston 620 that can freely reciprocate within a compatible hollow cylinder 622. For clutching, piston 618 is selectively pushed from the outside toward sheath-covered-sleeve 20 by a controlled pressurized air (or another hydraulic fluid) through port 624 to clasp housing 604 onto sheath-sleeve 30. For releasing the clutch, piston 618 is selectively pulled away from sheath-covered-sleeve 20 by suction of the controlled pressurized air through port 624.

Figure 26A:
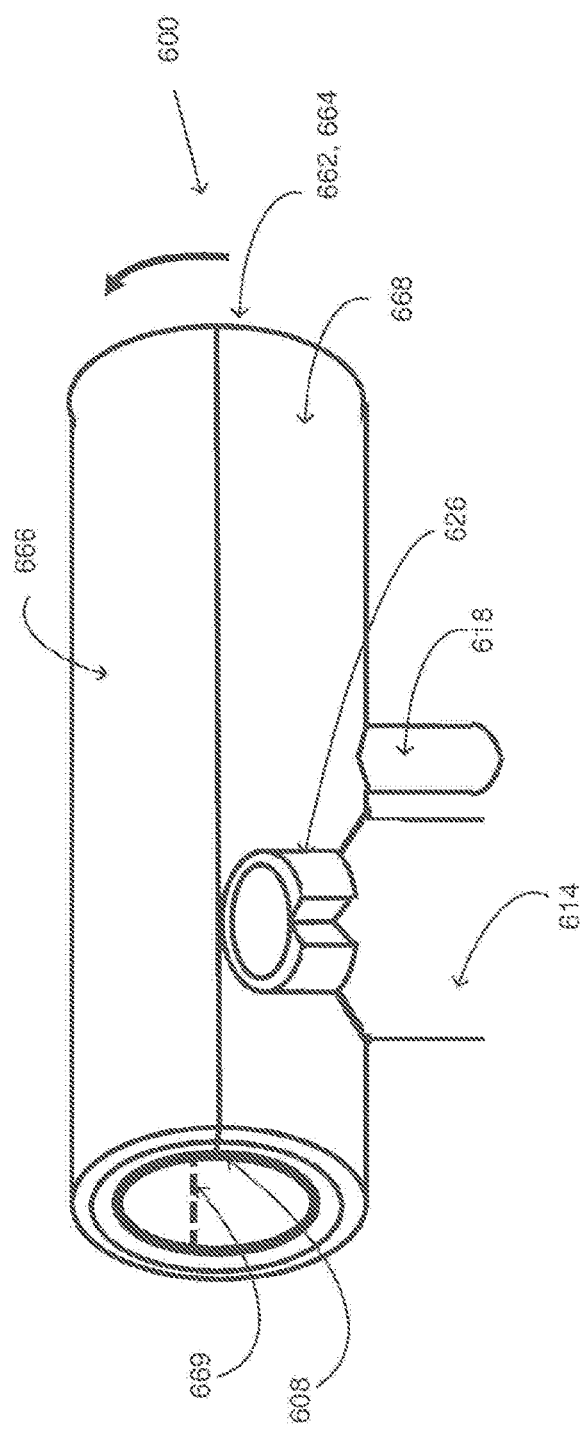
FIGS. 26A and 26B are schematic isometric illustrations, of a modification of the endoscope adapter of FIGS. 24A and 24B, exemplifying a closed state and an open state, respectively.
Figure 26B:
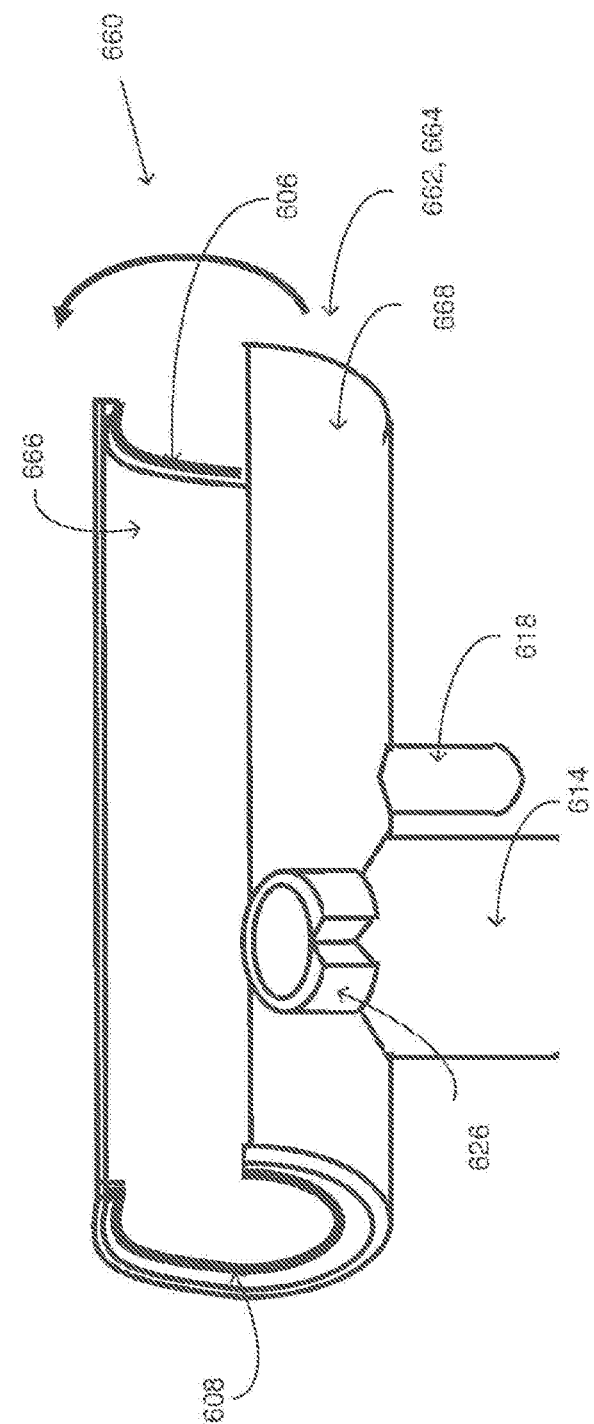

FIGS. 26A and 26B are schematic isometric illustrations, of a modification of endoscope adapter 600 of FIGS. 24A and 24B, featuring endoscopic adapter 660, and exemplifying a closed state and an open state, respectively. Adapter housing 662 in FIGS. 26A and 26B features tubular shell 664 that covers proximal end 22 of sleeve-covered-sheath 20. Shell 628 includes two portions 666 and 668, that can be releasably secured to each other, e.g., by pivoting about hinge 669, to form the tubular shell structure of shell 662 while being fastened about and around sleeve-covered-sheath 20.

FIGS. 27A and 27B are schematic isometric illustrations of a modification of endoscope adapter 600 of FIGS. 24A and 24B, featuring endoscopic adapter 670, and exemplifying a contracted state and an extended state, respectively. Adapter housing 672 includes a flexible proximal tubular portion 674 that allows extension and contraction thereof and thereby of housing 672 to facilitate free insertion and retraction movement of endoscope 81 within sleeve-covered-sheath 20 while keeping a distal end 677 (e.g., formed with endoscope sealing ring 608) of housing 672 sealingly engaging sheath sleeve 30. Likewise, endoscope sealing ring 606 may similarly keep proximal end 676 of housing 672 sealingly engaging endoscope 81. It is noted that the term 'engaging' refers to fixedly attaching as well as to slidingly coupling—which may be necessary during the insertion or retraction movement of endoscope 81 within housing 674 or when housing 764 is slid along sheath 20.

Figure 28:
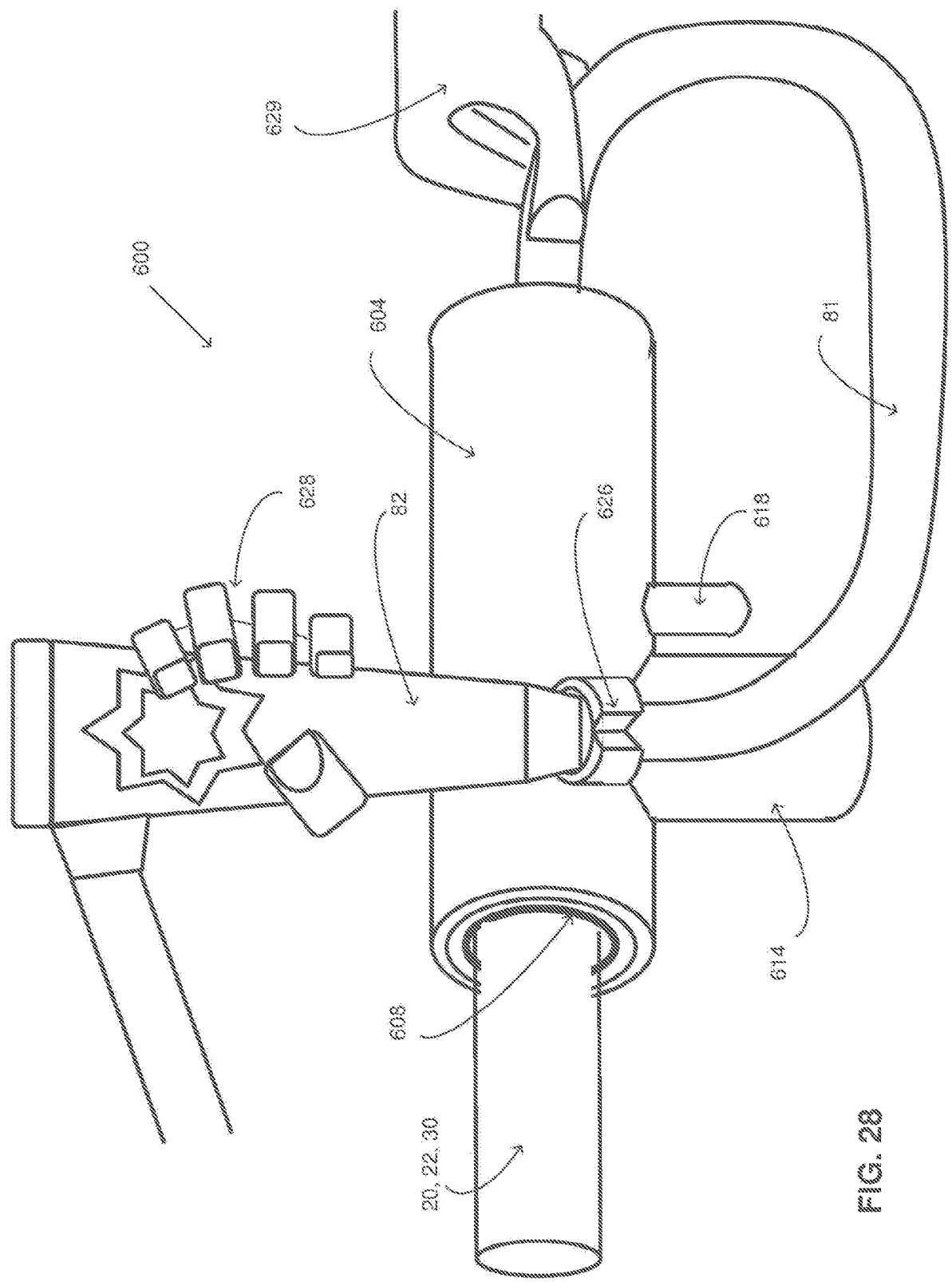
FIG. 28 is a schematic isometric sectional illustration of endoscope adapter of FIGS. 24A and 24B, exemplifying placement of an endoscope handle in an endoscope handle fastening fixture.

FIG. 28 is a schematic isometric sectional illustration of endoscope adapter 600 of FIGS. 24A and 24B, exemplifying placement of endoscope handle 82 in endoscope handle fastening fixture 626. Endoscope handle fastening fixture 626 is mounted on adapter housing 604 for convenience of the user, whose left hand 628 and right hand 629 are exemplified, by allowing placement of endoscope handle 82 therein. Fastening fixture 626 may incorporate some flexibility for effectively gripping handle 82 when nested in fixture 626.

Figure 29:
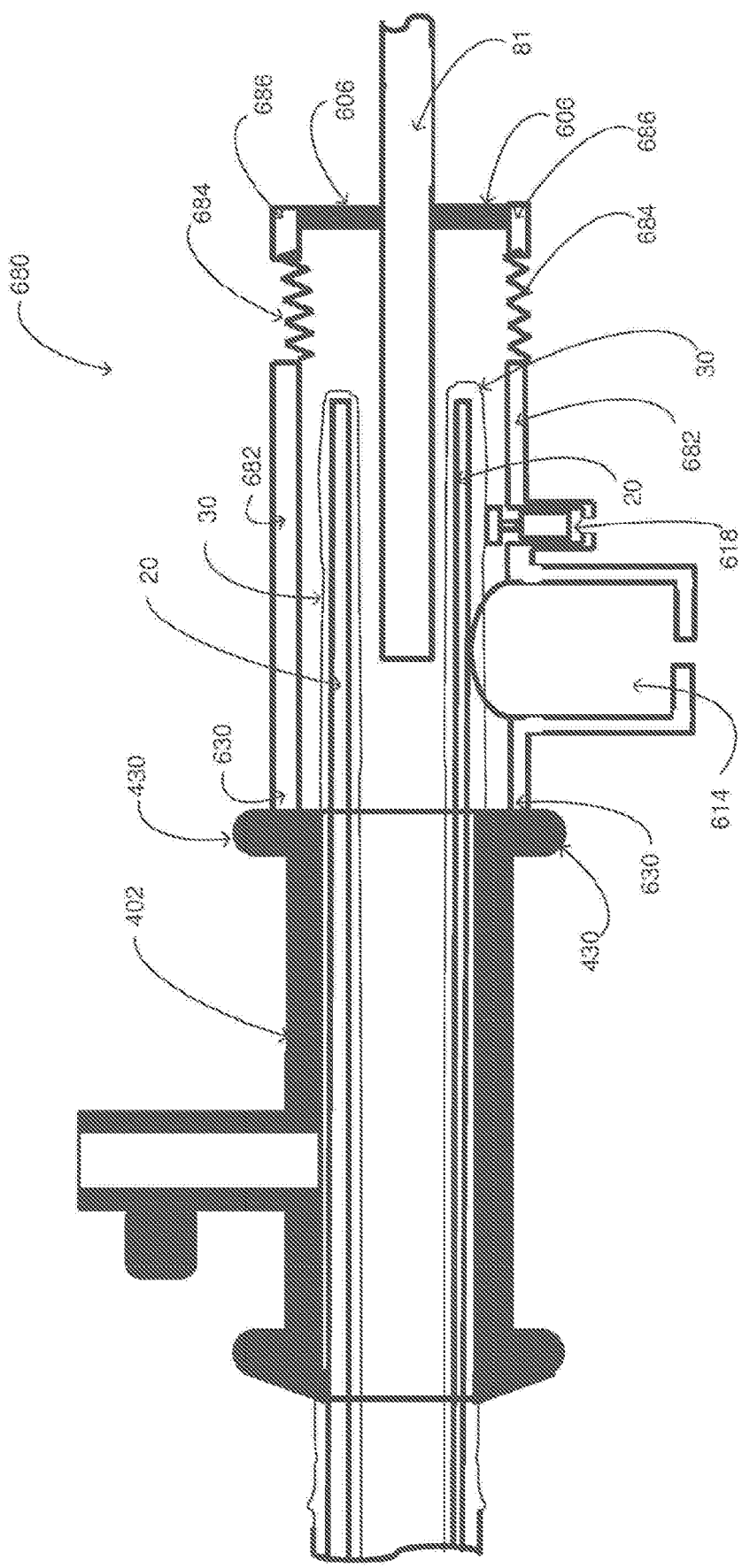
FIG. 29 is a schematic cross-sectional illustration of another embodiment of an endoscope adapter, constructed and operative in accordance with the invention.
Figure 30:
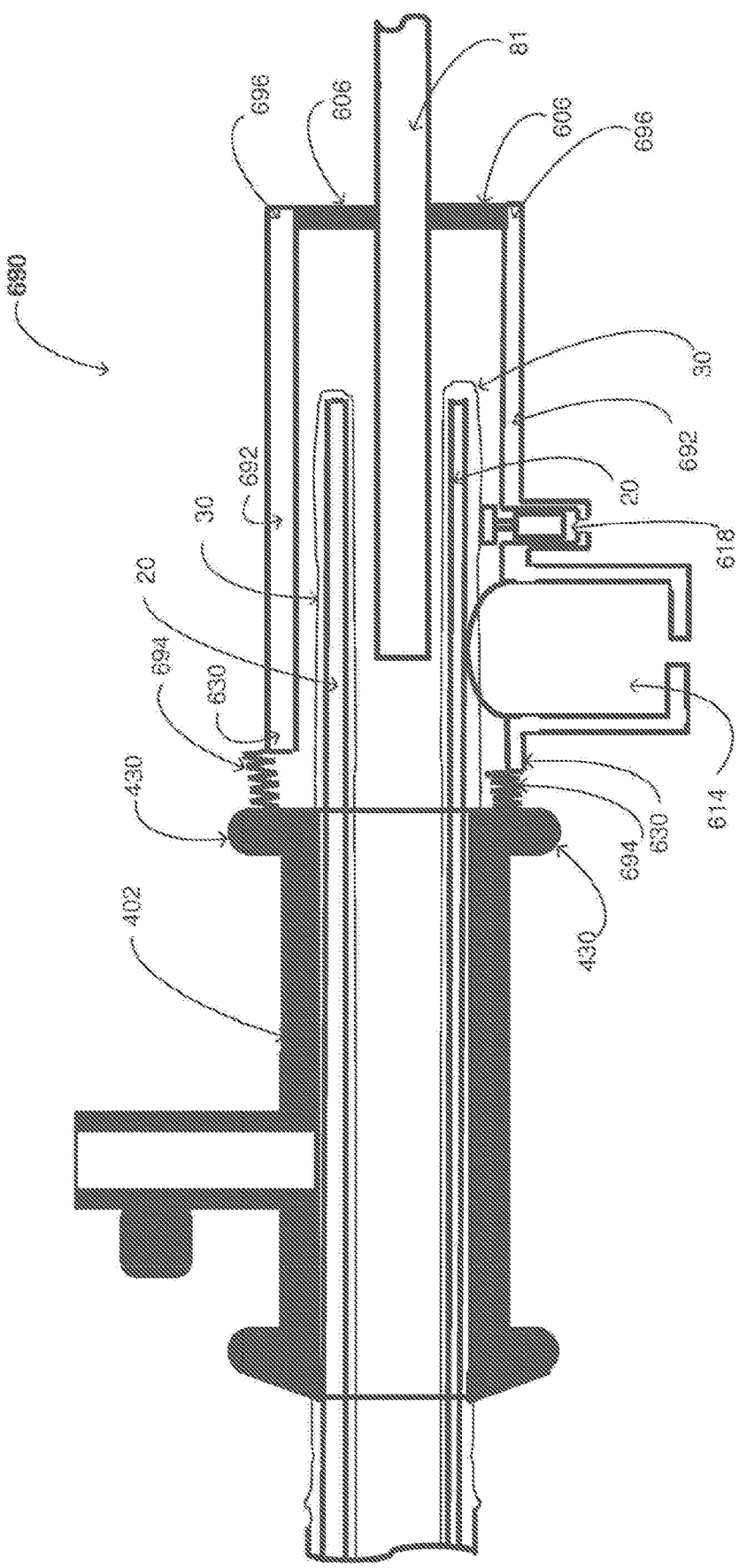
FIG. 30 is a schematic cross-sectional illustration of a further embodiment of an endoscope adapter, constructed and operative in accordance with the invention.

Optionally, the adapter may be sealingly coupled to a proximal end of the valve unit. Such an adapter may include a flexible portion that allows extension and contraction thereof to facilitate free insertion and retraction movement of the endoscope within the sleeve-covered-sheath and the adapter. The flexible portion may form a proximal or a distal portion of the adapter or sealingly couple the adapter to the valve unit. Reference is now made to FIGS. 29 and 30. FIG. 29 is a schematic cross-sectional illustration of another embodiment of an endoscope adapter denoted 680, constructed and operative in accordance with the invention. Adapter 680 is a modification of endoscope adapter 670 of FIGS. 27A and 27B, featuring direct coupling of its distal end 630 to proximal end 430 of valve unit 402 (which may be similar to valve unit 40 or 400). This coupling is sealingly hermetical to avoid leakage of fluids at the coupling and obviates the need of installing a redundant gasket between adapter housing 682 and sleeve-covered-sheath 20. The coupling of adapter housing 682 to valve unit 402, is a mountings adapter 680 to unit 402 such that both are fixedly stabilized to each other. Adapter housing 682 includes a flexible proximal tubular portion 684 that allows extension and contraction thereof and thereby of the proximal side of housing 682 to facilitate free insertion and retraction movement of endoscope 81 within sleeve-covered-sheath 20 and housing 682. Flexible proximal tubular portion 684 is impermeable to body fluids and while proximal end 686 of housing 682 is sealingly engaging endoscope 81 with endoscope sealing ring 606 to avoid body fluids leakage. It is noted that a flexible tubular alternative portion similar to flexible proximal tubular portion 684 may be applied in lieu of portion 684, wherein such an alternative portion may be disposed at a distal location in housing 682.

FIG. 30 is a schematic cross-sectional illustration of a further embodiment of an endoscope adapter denoted 690. constructed and operative in accordance with the invention. Adapter 690 is a further modification of endoscope adapter 670 of FIGS. 27A and 27B, featuring coupling of a distal end 630 of adapter housing 692 to proximal end 430 of valve unit 402, by means of a flexible distal tubular portion 694 that allows extension and contraction thereof, and thereby of adapter housing 692, to facilitate free insertion and retraction movement of endoscope 81 within sleeve-covered-sheath 20 and housing 692. Flexible distal tubular portion 694 is impermeable to body fluids and is sealingly coupled to proximal end 430 of valve unit 402 and to distal end 630 of adapter housing 682 to avoid leakage of body fluids. Such sealingly mounting, of adapter housing 692 to valve unit 402, obviates the need of installing a redundant gasket between adapter housing 682 and sleeve-covered-sheath 20. Endoscope sealing ring 606 keeps proximal end 696 of housing 692 sealingly engaging endoscope 81 to avoid leakage of body fluids.

Figure 31:
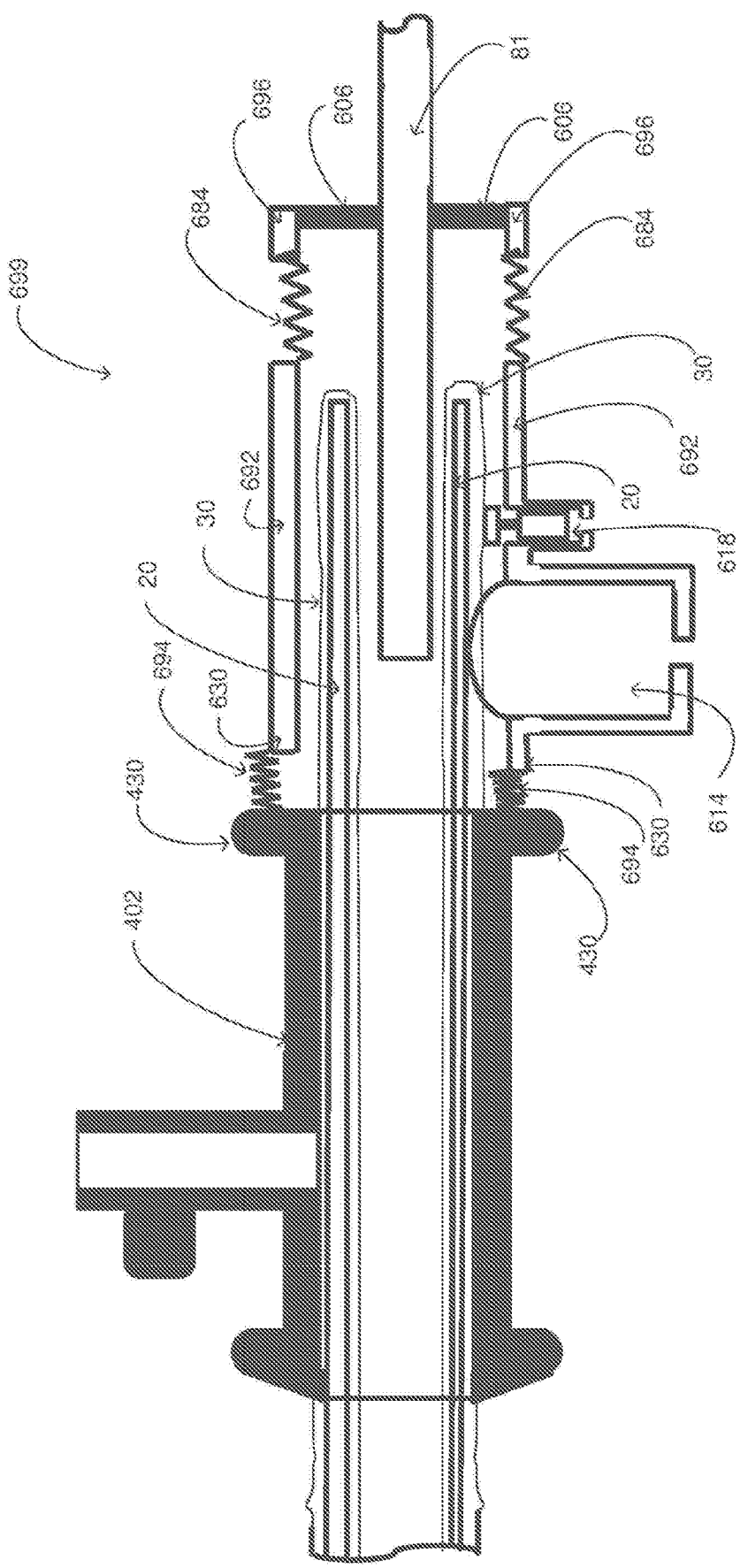
FIG. 31 is a schematic cross-sectional illustration of a further embodiment of an endoscope adapter, constructed and operative in accordance with the invention.

According to a further aspect of the invention, the endoscopic adapter may feature any and all of the flexible tubular portions described herein above (e.g., with respect to FIGS. 27A, 27B, 29, and 30). Any such flexible tubular portion facilitates free insertion and retraction movement of endoscope 81 within sleeve-covered-sheath 20, and within housing 672, 682, or 692, respectively, as well as adding freedom of movement of the proximal part of the corresponding housing (672, 682, 692) or of the entire housing 692, with respect to valve unit 402, which further facilitates free insertion and retraction movement of endoscope 81. FIG. 31 is a schematic cross-sectional illustration of a further embodiment of an endoscope adapter denoted 699, constructed and operative in accordance with the invention, which combines the flexible portions of the embodiments of FIGS. 29 and 30 and inherits their benefits. Adapter 699 includes all the features of adapter 690, which are similarly numbered (i.e., 20, 30, 81, 402, 430, 614, 618, 630, 692, 694, and 696), in addition to a flexible proximal tubular portion which resembles portion 684 of adapter 680 of FIG. 29, and is similarly numbered 684 accordingly (Adapter 699 also includes all the features of adapter 680, in addition to flexible distal tubular portion 694).

Figure 32:
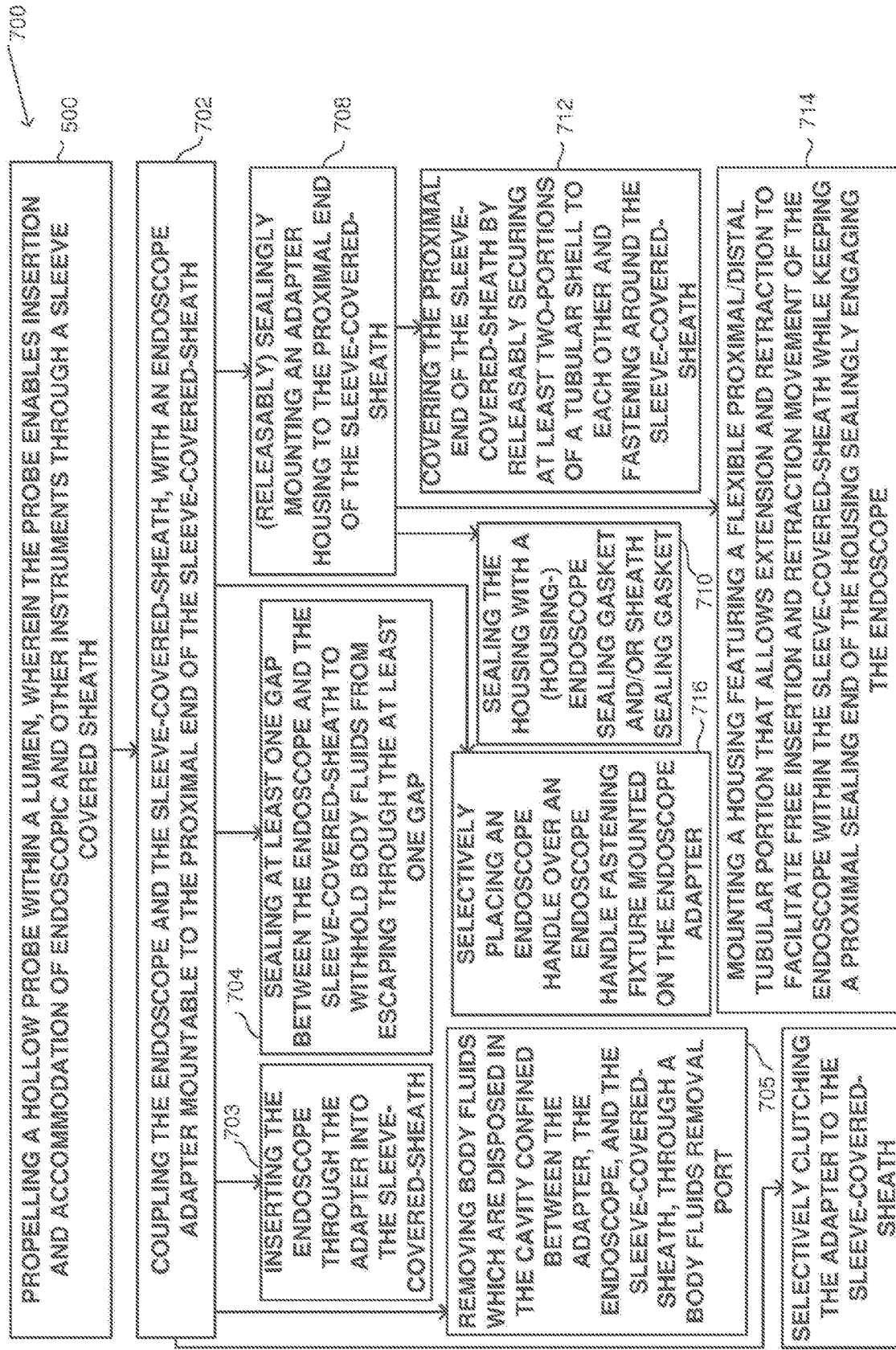
FIG. 32 is a block diagram of a method for operating an endoscope adapter, operative in accordance with an embodiment of the disclosed invention.

In reference to FIG. 32, there is shown a block diagram of method 700 for operating an endoscope adapter, operative in accordance with an embodiment of the disclosed invention.

Method 700 includes the procedures of method 500 for propelling a hollow probe within a lumen, wherein the probe enables insertion and accommodation of endoscopic and other instruments ("endoscope"). In addition to the procedures of method 500, method 700 further includes procedure 702 of coupling the endoscope and the sleeve-covered-sheath, with an endoscope adapter mountable to the proximal end of the sleeve-covered-sheath. The coupling is performed by an endoscope adapter mountable to the proximal end of the sleeve-covered-sheath and allowing insertion of the endoscope through the adapter into the sleeve-covered-sheath, for retaining body fluids from escaping through the gap. In reference to FIGS. 24A-25B, endoscope 81 and sleeve-covered-sheath 20 are coupled by endoscope adapter 650 which mountable to proximal end 22 of sleeve-covered-sheath 20.

Procedure 702 of coupling includes sub-procedure 703 of inserting the endoscope through the adapter into the sleeve-covered-sheath. In reference to FIGS. 24A-25B, endoscope 81 is inserted through adapter 600 into sleeve-covered-sheath 20.

Procedure 702 of coupling includes sub-procedure 704 of sealing at least one gap between the endoscope and the sleeve-covered-sheath to withhold body fluids from escaping through the at least one gap. In reference to FIGS. 24A-25B, at least one gap between endoscope 81 and sleeve-covered-sheath 20, is sealed by gaskets 606 and 608, or ring 652, to withhold body fluids from escaping through the at least one gap.

Procedure 702 of coupling may include sub-procedure 705 of removing body fluids which are disposed in the cavity confined between the adapter, the endoscope, and the sleeve-covered-sheath, through a body fluids removal port. In reference to FIGS. 24A-25B, body fluids which are disposed in cavity 612, which is confined between adapter 600, endoscope 81, and sleeve-covered-sheath 20, are removed through body fluids removal port 614.

Procedure 702 of coupling may include sub-procedure 706 of selectively clutching the adapter to the sheath sleeve. In reference to FIGS. 24A-25B, adapter 600 is selectively clutched to sheath sleeve 30 by clutch 618.

Procedure 702 of sealing may include sub-procedure 708 of (releasably) sealingly mounting an adapter housing to the proximal end of the sleeve-covered-sheath. In addition, the adapter housing may be also mounted to a valve unit serving the sleeve-covered sheath. Sub-procedure 708 of sealingly mounting may further include sub-procedure 710 of sealing the housing with a housing-endoscope sealing gasket and a housing-sheath sealing gasket. In this case, sub-procedures 708 and 710 are an example of implementing sub-procedure 704 and as such replace sub-procedure 704. In reference to FIGS. 24A-25B, adapter housing 604 is (releasably) sealingly mounted to proximal end 22 of sleeve-covered-sheath 20. Housing 604 is sealed with housing-endoscope sealing gasket 606 and housing-sheath sealing gasket 608. In reference to FIGS. 28-29, Housings 682 or 692 are mounted to valve unit 402.

Sub procedure 708 of sealingly mounting may further include sub-procedure 712 of covering the proximal end of the sleeve-covered-sheath by releasably securing at least two-portions of a tubular shell to each other and fastening around the sleeve-covered-sheath. In reference to FIGS. 26A-26B, proximal end 22 of sleeve-covered-sheath 20 is covered by releasably securing two-portions 666 and 668 of tubular shell 664 to each other and fastening around sleeve-covered-sheath 20.

Sub procedure 708 of sealingly mounting may further include sub procedure 714 of mounting a housing featuring a flexible proximal or distal tubular portion that allows extension and retraction to facilitate free insertion and retraction movement of the endoscope within the sleeve-covered-sheath while keeping a distal end of the housing sealingly engaging the sheath sleeve (and while keeping a proximal end of the housing sealingly engaging the endoscope). In reference to FIGS. 27A-27B, housing 672 is mounted to sheath 20 and features a flexible proximal tubular portion 674 that allows extension and retraction to facilitate free insertion and retraction movement of endoscope 81 within sleeve-covered-sheath 20 while keeping distal end 630 of housing 672 sealingly engaging sheath sleeve 30 (and while keeping proximal end 676 of housing sealingly engaging endoscope 81). In reference to FIGS. 29-31, housings 682, 684 are mounted to sheath valve unit 402 and feature a flexible proximal tubular portion 684, 694, respectively, that allows extension and retraction to facilitate free insertion and retraction movement of endoscope 81 within sleeve-covered-sheath 20 and housing 682 or 692, while keeping distal end 630 of housing 672 sealingly coupled with proximal end 430 of valve unit 402, and while keeping proximal end 686 or 696 sealingly engaging endoscope 81. In FIGS. 30 and 31, flexible portion 694 is also operational for sealingly coupling housing 692 to valve unit 402.

Method 700 may further include procedure 716 of selectively placing an endoscope handle over an endoscope handle fastening fixture mounted on the endoscope adapter. In reference to FIG. 28, endoscope handle 82 is selectively placed over endoscope handle fastening fixture 626 which is mounted on endoscope adapter 600.

Although preferred embodiments are described hereinabove with reference to a device for moving an instrument through the lower gastrointestinal tract, it will be understood that the novel principles of the present invention may be used to move objects in other body cavities, such as, the throat or lungs, and may also be used to move objects in lumens and other regions for non-medical applications, as well. It is also understood that while the preferred embodiments described hereinabove have physical data leads and control leads, the propulsion and instrument package can be powered by batteries and can store data and/or transmit data by wireless communications, as is known in the art.

It will thus be appreciated that the preferred embodiments are cited herein by way of example, and the full scope of the invention is limited only by the claims.

While certain embodiments of the disclosed subject matter have been described, so as to enable one of skill in the art to practice the present invention, the preceding description is intended to be exemplary only. It should not be used to limit the scope of the disclosed subject matter, which should be determined by reference to the following claims.

The invention claimed is:

1. A hollow probe enabling insertion and accommodation of an endoscope, to be advanced or retracted within a lumen of a body, the hollow probe comprising:
   a central valve unit comprising a central bore having a proximal end and a distal end, and at least one valve for controlling the introduction and withdrawal of an inflating/deflating fluid into said central bore;
   a sliding tubular sheath movably disposed inside the central bore of said central valve unit;
   a flexible sleeve, impermeable to said inflating/deflating fluid and sealingly anchored to said central valve unit on both said distal end and said proximal end, said sleeve being folded over to cover both inside and outside of said sheath to sealingly envelop said sheath together with said central valve unit to produce a sleeve-covered-sheath, the sleeve configured to contain said inflating/deflating fluid, while allowing sliding movement of the sleeve-covered-sheath within said central bore; and
   an endoscope adapter, comprising an adapter housing, sealingly mounted to the proximal end of said sleeve-covered-sheath and sealingly coupled to the proximal end of said central valve unit, the endoscope adapter configured to allow insertion of said endoscope through the endoscope adapter into said sleeve-covered-sheath, the endoscope adapter further comprising at least one gasket configured to seal at least one gap between said endoscope adapter and said endoscope or said sleeve-covered-sheath for withholding body fluids from escaping through said at least one gap, the endoscope adapter further comprising a flexible portion, configured for extension and contraction for extending and contracting said adapter housing to facilitate free insertion and retraction movement of said endoscope within said sleeve-covered-sheath.

2. The hollow probe according to claim 1, wherein said endoscope adapter comprises a body fluids removal port configured to allow removal of said body fluids when disposed in a cavity confined between said endoscope adapter, said endoscope, and said sleeve-covered-sheath.

3. The hollow probe according to claim 1, wherein said endoscope adapter comprises a clutch configured to selectively clasp at least one of said sleeve and said sleeve-covered-sheath.

4. The hollow probe according to claim 1, wherein said at least one gasket comprises at least one of:
   a housing-endoscope sealing gasket, configured to seal a gap between a proximal side of said adapter housing and said endoscope; and
   a housing-sheath sealing gasket, to seal a gap between a distal side of said adapter housing and said sleeve-covered-sheath.

5. The hollow probe according to claim 1, wherein said endoscope adapter comprises an endoscope handle fastening fixture for allowing placement of an endoscope handle.

6. The hollow probe according to claim 1, wherein said adapter housing comprises a tubular shell that covers said proximal end of said sleeve-covered-sheath, wherein said shell comprises at least two portions that can be releasably secured to each other to form said tubular shell and to be fastened around said sleeve-covered-sheath.

7. The hollow probe according to claim 1, wherein a distal sealing end of said adapter housing is sealingly engaged with said sleeve, and wherein a proximal end of said adapter housing is sealingly engaged with said endoscope.

8. The hollow probe according to claim 1 wherein said flexible portion of the endoscope adapter comprises at least one of:
   a flexible proximal portion;
   a flexible distal portion; and
   a flexible portion sealingly coupled with a distal end of said adapter housing and a proximal end of said central valve unit.

9. A method for propelling a hollow probe within a lumen of a body, the probe enabling insertion and accommodation of an endoscope to be advanced or retracted within the lumen, the method comprising procedures of:
   inserting a flexible sleeve within a tubular sheath;
   sliding said sheath within a central bore of a central valve unit;
   folding over a proximal sleeve portion and a distal sleeve portion of said sleeve over both ends of said sheath to cover both inside and outside of a proximal sheath portion and a distal sheath portion of said sheath;
   anchoring said proximal sleeve portion to a proximal end of said central bore and anchoring said distal sleeve portion to a distal end of said central bore, such that said sleeve together with said central valve unit sealingly envelop said sheath to produce a sleeve-covered-sheath;

inserting a distal tip portion of said sleeve-covered-sheath into said lumen;

advancing and retracting said sheath within said lumen while maintaining said sheath covered by said sleeve; and sealingly mounting an adapter housing of an endoscope adapter to a proximal end of the sleeve-covered-sheath and sealingly coupling said adapter housing to a proximal end of said central valve unit;

inserting said endoscope through said endoscope adapter into said sleeve-covered-sheath;

sealing at least one gap between said endoscope adapter and said endoscope or said sleeve-covered-sheath to withhold body fluids from escaping through said, using at least one gasket of said endoscope adapter;

extending and contracting a flexible portion of the endoscope adapter for extending and contracting said adapter housing to facilitate free insertion and retraction movement of said endoscope within said sleeve-covered-sheath; and selectively inflating or deflating said sleeve for advancing or receding said sheath or for inserting, retracting or operating said endoscope, by introducing or withdrawing an inflating/deflating fluid into said central bore through at least one valve of said central valve unit.

10. The method for propelling a hollow probe within a lumen as in claim 9, comprising removing said body fluids when disposed in a cavity confined between said endoscope adapter, said endoscope, and said sleeve-covered-sheath, through a body fluids removal port of said endoscope adapter.

11. The method for propelling a hollow probe within a lumen as in claim 9, wherein said procedure of sealing at least one gap comprises at least one of:

sealing a gap between a proximal side of said adapter housing and said endoscope with a housing-endoscope sealing gasket, and sealing a gap between a distal side of said adapter housing and said sleeve-covered-sheath with a housing-sheath sealing gasket.

12. The method for propelling a hollow probe within a lumen as in claim 9, further comprising the procedure of selectively placing an endoscope handle over an endoscope handle fastening fixture mounted on said endoscope adapter.

13. The method for propelling a hollow probe within a lumen as in claim 9, wherein said procedure of sealingly mounting further comprises covering said proximal end of said sleeve-covered-sheath by releasably securing at least two portions of a tubular shell of said adapter housing to each other and fastening around said sleeve-covered-sheath.

14. The method for propelling a hollow probe within a lumen as in claim 9, wherein said procedure of sealingly mounting further comprises keeping a distal sealing end of said adapter housing sealingly engaging said sleeve and keeping a proximal end of said adapter housing sealingly engaging said endoscope.

* * * * *